United States Patent
Ftouni

(10) Patent No.: US 12,357,976 B2
(45) Date of Patent: Jul. 15, 2025

(54) GNCC AND/OR PCC AS A CATALYTIC CARRIER FOR METAL SPECIES

(71) Applicant: OMYA INTERNATIONAL AG, Oftringen (CH)

(72) Inventor: Jamal Ftouni, Zofingen (CH)

(73) Assignee: Omya International AG, Oftringen (CH)

( * ) Notice: Subject to any disclaimer, the term of this patent is extended or adjusted under 35 U.S.C. 154(b) by 673 days.

(21) Appl. No.: 17/753,938

(22) PCT Filed: Sep. 23, 2020

(86) PCT No.: PCT/EP2020/076560
§ 371 (c)(1),
(2) Date: Mar. 18, 2022

(87) PCT Pub. No.: WO2021/058558
PCT Pub. Date: Apr. 1, 2021

(65) Prior Publication Data
US 2023/0347325 A1    Nov. 2, 2023

(30) Foreign Application Priority Data
Sep. 26, 2019 (EP) .................................. 19199927

(51) Int. Cl.
| | |
|---|---|
| *B01J 27/232* | (2006.01) |
| *B01J 23/46* | (2006.01) |
| *B01J 35/40* | (2024.01) |
| *B01J 35/61* | (2024.01) |
| *B01J 37/00* | (2006.01) |
| *B01J 37/08* | (2006.01) |
| *B01J 37/18* | (2006.01) |

(52) U.S. Cl.
CPC ........... *B01J 27/232* (2013.01); *B01J 23/462* (2013.01); *B01J 35/40* (2024.01); *B01J 35/612* (2024.01); *B01J 35/613* (2024.01); *B01J 37/0045* (2013.01); *B01J 37/08* (2013.01); *B01J 37/18* (2013.01)

(58) Field of Classification Search
CPC ...... B01J 27/232; B01J 35/613; B01J 35/612; B01J 35/40; B01J 23/462; B01J 37/0045; B01J 37/08; B01J 37/16; B01J 37/18
USPC ................................................. 502/325, 326
See application file for complete search history.

(56) References Cited

U.S. PATENT DOCUMENTS

| | | | |
|---|---|---|---|
| 5,703,254 A | 12/1997 | Gaffney et al. | |
| 5,965,480 A | 10/1999 | Cooker et al. | |
| 10,875,014 B2 * | 12/2020 | Gane | C09C 1/021 |
| 2019/0381484 A1 * | 12/2019 | Ha | B01J 23/462 |

FOREIGN PATENT DOCUMENTS

| | | | |
|---|---|---|---|
| CN | 101947445 A | 1/2011 | |
| EP | 2080738 A1 | 7/2009 | |
| EP | 2371766 A1 | 10/2011 | |
| EP | 2447213 A1 | 5/2012 | |
| EP | 2524898 A1 | 11/2012 | |
| EP | 2840065 A1 | 2/2015 | |
| EP | 3275537 A1 | 1/2018 | |
| EP | 3599223 A1 | 1/2020 | |
| WO | 2004030813 A1 | 4/2004 | |
| WO | WO-2008069991 A1 * | 6/2008 | ............ C07C 29/60 |
| WO | 2013142473 A1 | 9/2013 | |
| WO | 2013190076 A1 | 12/2013 | |
| WO | 2019174928 A1 | 9/2019 | |

OTHER PUBLICATIONS

Jeroen ten DAM et al.; Tuning selectivity of Pt/CaCO3 in glycerol hydrogenolysis—A Design of Experiments approach; Catalysis Communications Journal, vol. 13, No. 1 (Jun. 2011) pp. 1-5; Biocatalysis and Organic Chemistry, Department of Biotechnology, Delft University of Technology, Julianalaan 136, 2628 BL Delft, The Netherlands; Catalysis Engineering, Department of Chemical Engineering, Delft University of Technology, Julianalaan 136, 2628 BL Delft, The Netherlands.

International Search Report and Written Opinion issued in PCT/EP2020/076560 mailed Nov. 19, 2020.

Chengxiong Dang et al., "Syngas production by dry reforming of the mixture of glycerol and ethanol with CaC03," Journal of Energy Chemistry, vol. 43, Aug. 7, 2019, pp. 90-97, Elsevier, Amsterdam, NL.

Chunli Xu et al., "Insight into effect of acid/base nature of supports on selectivity of glycerol oxidation over supported Au—Pt bilnetallic catalysts," Applied Catalysis B: Environmental, vol. 164, Mar. 1, 2015, pp. 334-343, Elsevier, Amsterdam, NL.

Jeroen ten DAM et al., "Tuning selectivity of Pt/CaCO3 in glycerol hydrogenolysis—A Design of Experiments approach," Catalysis Communications, vol. 3, No. 1, Jun. 6, 2011, pp. 1-5, Elsevier, Amsterdam, NL.

* cited by examiner

*Primary Examiner* — Patricia L. Hailey
(74) *Attorney, Agent, or Firm* — Heslin Rothenberg Farley & Mesiti P.C.

(57) ABSTRACT

The present invention refers to a catalytic system comprising a transition metal compound on a solid carrier, wherein the content of the transition metal compound on the surface of the solid carrier is from 0.1 to 30 wt.-%, based on the dry weight of the solid carrier. Furthermore, the present invention refers to a method for manufacturing the catalytic system, the use of the inventive catalytic system in a chemical reaction, the use of a solid carrier loaded with a transition metal compound as a catalyst and to granules mouldings or extrudates comprising the catalytic system.

20 Claims, No Drawings

GNCC AND/OR PCC AS A CATALYTIC CARRIER FOR METAL SPECIES

CROSS REFERENCE TO RELATED APPLICATIONS

This application is a U.S. National Phase filing under 35 U.S.C. § 371 of International Application PCT/EP2020/076560, filed Sep. 23, 2020, and published as WO 2021/058558 A1 on Apr. 1, 2021. PCT/EP2020/076560 claims priority from European patent application number 19199927.5, filed Sep. 26, 2019. The entire contents of each of these prior applications are hereby incorporated herein by reference.

The present invention refers to a catalytic system comprising a transition metal compound on a solid carrier, wherein the content of the transition metal species on the surface of the solid carrier is from 0.1 to 30 wt.-%, based on the dry weight of the solid carrier. Furthermore, the present invention refers to a method for manufacturing the catalytic system, the use of the inventive catalytic system in a chemical reaction, the use of a solid carrier loaded with a transition metal compound as a catalyst and to granules mouldings or extrudates comprising the catalytic system.

Catalyst or catalytic systems comprising a carrier and a catalyst are widely used in catalysis and have several advantages. For example, the handling of such catalytic systems and also the isolation of reaction products is less expensive compared with homogeneous systems. Furthermore, the activity and efficiency of a catalytic system in a given reaction may be controlled by selecting specific structural properties of the carrier or a specific transition metal.

Elemental transition metals and corresponding compounds, such as transition metal salts, oxides or complexes, are well-known catalysts and may be applied in a number of reactions, for example in alkene or alkyne hydrogenation or in epoxidation. Some of the most frequently used transition metals include platinum, palladium and copper.

Common support materials for heterogeneous transition metal catalysis are activated carbon, carbon black/graphite, alumina, barium sulphate and calcium carbonate (The Catalyst Technical Handbook, Johnson Matthey Co., 2005).

For example, U.S. Pat. Nos. 5,965,480 and 5,703,254 disclose the direct oxidation of propylene to propylene oxide using silver catalysts on alkaline earth metal carbonate-containing carriers, such as calcium carbonate, to catalyse selectively the formation of epoxides.

WO 2004/030813 A1 relates to a process for preparing a catalyst which involves (a) preparing a paste having a uniform mixture of at least one alkaline earth metal carbonate, a liquid medium, a silver bonding additive, and at least one extrusion aid and/or optionally a burnout additive; (b) forming one or more shaped particles from the paste; (c) drying and calcining the particles; and (e) impregnating the dried and calcined particles with a solution containing a silver compound. Said alkaline earth metal carbonate may be calcium carbonate.

WO 2013/190076 A1 relates to a catalytic system, which is a Lindlar type catalyst, wherein the support material (calcium carbonate) has an average particle size (d50) of more than 10 μm. It further discloses the use of such a catalytic system for the partial hydrogenation of a carbon-carbon triple bond to a double bond. Specific examples of carrier materials include precipitated calcium carbonate.

WO2019/174928 A1 refers to antimicrobial particulate compositions and a personal care composition comprising the same. The compositions comprise calcite and antimicrobial particles. The particles can be silver or copper particles and are present in the composition up to 3 wt.-%.

However, transition metal compounds are only rare available in natural resources and, therefore, high costs for procurement and recycling, if possible at all, incur. Another drawback is the toxicity of transition metals and corresponding salts and, therefore, the catalyst loadings in transition metal-catalysed reactions should be kept as low as possible. Accordingly, there is a continuous need for the improvement of catalytic systems to overcome one or more of the aforementioned drawbacks.

One object of the present invention may therefore be seen in the provision of a more efficient catalytic system, which allows to reduce the catalyst loading during catalysis and the overall consumption of transition metals and allows to obtain a specific compound, i.e. a product with high selectivity. A further object of the present invention may be seen in the provision of a time-saving catalytic system with higher turnover rates. Yet one further object may be seen in the provision of an easily recyclable catalytic system to reduce the overall consumption of transition metals. One further object may therefore be seen in the provision of a more environmentally compatible catalytic system. Finally, one further object of the present invention may be seen in the use of a carrier obtained naturally or using a sustainable chemical process, starting from sustainable sources.

The foregoing and other problems may be solved by the subject-matter as defined herein in the independent claims.

A first aspect of the present invention relates to a catalytic system comprising a transition metal compound on a solid carrier, wherein a) the solid carrier is a ground natural calcium carbonate (GNCC) and/or precipitated calcium carbonate (PCC) and has a specific surface area of from 3 to 50 $m^2/g$ measured using nitrogen and the BET method according to ISO 9277:2010; and b) wherein the transition metal compound is selected from the group consisting of elemental Ni, elemental Ru, elemental Au, elemental Fe, elemental Cu, oxides of the foregoing transition metal compounds and mixtures thereof;

and wherein the content of the transition metal species on the surface of the solid carrier is from 0.1 to 30 wt.-%, based on the dry weight of the solid carrier.

The inventors of the present application surprisingly found that the use of ground natural calcium carbonate (GNCC) and/or precipitated calcium carbonate (PCC) as catalyst carrier in transition metal catalysis, wherein the transition metal compound is selected from the group consisting of elemental Ni, elemental Ru, elemental Au, elemental Fe, elemental Cu, oxides of the foregoing transition metal compounds and mixtures thereof provides several advantages.

First of all, ground natural calcium carbonate (GNCC) or precipitated calcium carbonate (PCC) are easily and cheap obtainable materials. Said material have found to be surprisingly useful as carrier material in catalysis.

In combination with the above mentioned transition metal compound, for example, higher catalytic activities, for example higher glycerol transformation under inert atmosphere, hydrogen or oxygen were achieved with the catalytic systems according to the present invention. Moreover, the inventive catalytic system may be easier to recover and higher yields may be achieved.

Another aspect of the present invention relates to a method for manufacturing a catalytic system comprising a transition metal compound on a solid carrier, the method comprising the following steps:
(a) providing at least one solid carrier, wherein the solid carrier is ground natural calcium carbonate (GNCC) and/or precipitated calcium carbonate (PCC) and has a specific surface area of from 3 to 50 m$^2$/g measured using nitrogen and the BET method according to ISO 9277:2010;
(b) providing at least one transition metal reagent comprising Ni ions, Ru ions, Au ions, Fe ions, Cu ions and mixtures thereof, in such an amount that the amount of said ions is from 0.1 to 30 wt.-%, based on the dry weight of the solid carrier;
(c) contacting the at least one solid carrier provided in step (a) and the transition metal reagent provided in step (b) to obtain a mixture comprising a solid carrier and a transition metal reagent; and
(d) calcining the mixture of step (c) at a temperature between 250° C. and 500° C. for obtaining a catalytic system comprising a transition metal compound on the solid carrier, wherein the transition metal compound is selected from the group consisting of Ni oxides, Ru oxides, Au oxides, Fe oxides, Cu oxides and mixtures thereof.

The inventors surprisingly found that by the above method it is possible to provide a catalytic system wherein the transition metal compound that is selected from the group consisting of elemental Ni, elemental Ru, elemental Au, elemental Fe, elemental Cu, oxides of the foregoing transition metal compounds and mixtures thereof is located on the solid carrier, which is a ground natural calcium carbonate (GNCC) and/or precipitated calcium carbonate (PCC). Furthermore, the above method is a cheap and simple production process which provides the inventive catalytic system.

Another aspect of the present invention refers to the use of the inventive catalytic system in a process comprising the following steps:
(A) providing one or more reactants;
(B) providing said catalytic system according to any of claims 1 to 6;
(C) subjecting the one or more reactants provided in step (A) to a chemical reaction in liquid or gas phase under air, O$_2$ atmosphere, H$_2$ atmosphere, or inert atmosphere at a temperature between 75 and 300° C. in the presence of the catalytic system provided in step (B).

Another aspect of the present invention refers to the use of a solid carrier according to the present invention loaded with a transition metal compound according to the present invention as a catalyst.

Finally, another aspect of the present invention refers to granules, mouldings or extrudates comprising the inventive catalytic system.

It should be understood that for the purposes of the present invention, the following terms will have the following meanings:

A "catalyst system" or "catalytic system" in the meaning of the present invention is a system that increases the rate of a chemical reaction by adding such a substance/compound/system to the reactants (compounds that are converted during the reaction), wherein the substance/compound/system is not consumed in the catalysed reaction and can continue to act repeatedly. The chemical reactions occurs faster or has an improved yield in the presence of such a catalytic system because it provides an alternative reaction pathway with a lower activation energy than the non-catalysed mechanism.

A "transition metal reagent" in the meaning of the present invention is a reagent that comprises a transition metal in ionic form. A "transition metal compound" in the meaning of the present invention is a compound that comprises a transition metal in elemental or oxide form. A "transition metal species" in the meaning of the present invention refers to the transition metal in the transition metal compound and can be an elemental transition metal or a transition metal ion in the transition metal oxide. A "transition metal" is any element in the d-block of the periodic table, which includes groups 3 to 12 on the periodic table.

A "solid carrier" in the meaning of the present invention is to be understood as a substance which may be loaded with a second substance (for example, transition metal compound) for the purpose of transporting said second substance to a target environment (for example, a reactor), for easily recuperating the catalytic system in the end of the process and for allowing a controlled size distribution of the metal species on the surface of the carrier in the preparation procedure. In the present invention the transition metal compound is located on the surface of the ground natural calcium carbonate and/or precipitated calcium carbonate.

"Ground natural calcium carbonate" (GNCC) in the meaning of the present invention is a calcium carbonate obtained from natural sources, such as limestone, marble, or chalk, and processed through a wet and/or dry treatment such as grinding, screening and/or fractionation, for example, by a cyclone or classifier.

"Precipitated calcium carbonate" (PCC) in the meaning of the present invention is a synthesised material, generally obtained by precipitation following a reaction of carbon dioxide and calcium hydroxide (hydrated lime) in an aqueous environment or by precipitation of a calcium- and a carbonate source in water. Additionally, precipitated calcium carbonate can also be the product of introducing calcium- and carbonate salts, calcium chloride and sodium carbonate for example, in an aqueous environment. PCC may have a vateritic, calcitic or aragonitic crystalline form. PCCs are described, for example, in EP 2 447 213 A1, EP 2 524 898 A1, EP 2 371 766 A1, EP 2 840 065 A1, or WO 2013/142473 A1.

The "particle size" of particulate materials herein is described by its distribution of particle sizes dx(wt). Therein, the value dx(wt) represents the diameter relative to which x % by weight of the particles have diameters less than dx(wt). This means that, for example, the d20(wt) value is the particle size at which 20 wt.-% of all particles are smaller than that particle size. The d50(wt) value is thus the weight median particle size, i.e. 50 wt.-% of all particles are smaller than that particle size. The measurement is made with a Sedigraph™ 5120 of Micromeritics Instrument Corporation, USA. The method and the instrument are known to the skilled person and are commonly used to determine particle size distributions. The measurement is carried out in an aqueous solution of 0.1 wt. % Na4P2O7. The samples are dispersed using a high speed stirrer and sonication.

Throughout the present document, the "specific surface area" (in m2/g) of ground natural calcium carbonate, precipitated calcium carbonate or other materials is determined using the BET method (using nitrogen as adsorbing gas), which is well known to the skilled man (ISO 9277:2010).

For the purpose of the present invention the "porosity" or "pore volume" refers to the intra-particle intruded specific pore volume. Said porosity or pore volume is measured using a Micromeritics Autopore V 9620 mercury porosimeter.

A "suspension" or "slurry" in the meaning of the present invention comprises insoluble solids and a liquid medium, for example water, and optionally further additives, and usually contains large amounts of solids and, thus, is more viscous and can be of higher density than the liquid from which it is formed.

The term "solid" according to the present invention refers to a material that is solid under standard ambient temperature and pressure (SATP) which refers to a temperature of 298.15 K (25° C.) and an absolute pressure of exactly 1 bar. The solid may be in the form of a powder, tablet, granules, flakes etc. Accordingly, the term "liquid medium" refers to a material that is liquid under standard ambient temperature and pressure (SATP) which refers to a temperature of 298.15 K (25° C.) and an absolute pressure of exactly 1 bar.

Where the term "comprising" is used in the present description and claims, it does not exclude other non-specified elements of major or minor functional importance. For the purposes of the present invention, the term "consisting of" is considered to be a preferred embodiment of the term "comprising". If hereinafter a group is defined to comprise at least a certain number of embodiments, this is also to be understood to disclose a group, which preferably consists only of these embodiments.

Whenever the terms "including" or "having" are used, these terms are meant to be equivalent to "comprising" as defined above.

Where an indefinite or definite article is used when referring to a singular noun, e.g. "a", "an" or "the", this includes a plural of that noun unless something else is specifically stated.

Terms like "obtainable" or "definable" and "obtained" or "defined" are used interchangeably. This, e.g., means that, unless the context clearly dictates otherwise, the term "obtained" does not mean to indicate that, e.g., an embodiment must be obtained by, e.g. the sequence of steps following the term "obtained" even though such a limited understanding is always included by the terms "obtained" or "defined" as a preferred embodiment.

Advantageous embodiments of the inventive catalytic system, the corresponding method of manufacturing said catalytic system and uses of said catalytic system are defined hereinafter as well as in the corresponding subclaims.

According to one embodiment of the present invention, the solid carrier is precipitated calcium carbonate (PCC).

According to another embodiment of the present invention, the solid carrier has:
  (i) a specific surface area in the range of from 5 to 40 m$^2$/g, preferably from 7 to 35 m$^2$/g and more preferably from 10 to 30 m$^2$/g, measured using nitrogen and the BET method according to ISO 9277:2010; and/or
  (ii) a $d_{50}$(wt) in the range of from 1 to 75 μm, preferably from 2 to 50 μm, more preferably from 3 to 40 μm, even more preferably from 4 to 30 μm and most preferably from 5 to 15 μm; and/or
  (iii) a $d_{98}$(wt) in the range of from 2 to 150 μm, preferably from 4 to 100 μm, more preferably from 6 to 80 μm, even more preferably from 8 to 60 μm and most preferably from 10 to 30 μm.

According to another embodiment of the present invention, the transition metal compound is selected from the group consisting of elemental Ni, NiO, Ni2O3, Ni3O4, elemental Ru, RuO2, Ru2O3, RuO4, elemental Au, Au2O, Au2O3, elemental Fe, FeO, FeO2, Fe2O3, Fe3O4, elemental Cu, CuO, Cu2O, CuO2, Cu2O3 and mixtures thereof, preferably is selected from the group consisting of elemental Ni, NiO, Ni2O3, Ni3O4, elemental Ru, RuO2, Ru2O3, RuO4, elemental Au, Au2O, Au2O3, elemental Cu, CuO, Cu2O, CuO2, Cu2O3 and mixtures thereof, more preferably is selected from the group consisting of elemental Ni, NiO, Ni2O3, Ni3O4, elemental Ru, RuO2, Ru2O3, RuO4, elemental Au, Au2O, Au2O3 and mixtures thereof and most preferably is selected from the group consisting of elemental Ru, RuO2, Ru2O3, RuO4 and mixtures thereof.

According to another embodiment of the present invention, the catalytic system further comprises one or more reaction products obtained by reaction of the combination of transition metal compound and the solid carrier.

According to another embodiment of the present invention, the content of the transition metal species on the surface of the solid carrier is in the range of from 0.25 to 25 wt. %, preferably from 0.5 to 20 wt. %, more preferably 1 to 15 wt. %, even more preferably from 2 to 10 wt. % and most preferably from 2.5 to 5 wt. %, based on the dry weight of the solid carrier.

According to another embodiment of the present invention, the method further comprises step (e) of reducing the calcined catalytic system obtained from step (d) under H2 atmosphere at a temperature between 100° C. and 500° C. for obtaining a catalytic system comprising a transition metal compound on the solid carrier, wherein the transition metal compound is selected from the group consisting of elemental Ni, elemental Ru, elemental Au, elemental Fe, elemental Cu, oxides of the foregoing transition metal compounds and mixtures thereof, preferably is selected from the group consisting of elemental Ni, elemental Ru, elemental Au, elemental Cu, oxides of the foregoing transition metal compounds and mixtures thereof and most preferably is selected from the group consisting of elemental Ni, elemental Ru, elemental Au, oxides of the foregoing transition metal compounds and mixtures thereof.

According to another embodiment of the present invention, the calcining step (d) is performed
  (i) under air, N$_2$ atmosphere, Ar atmosphere, O$_2$ atmosphere or mixtures thereof and/or
  (ii) at a temperature between 270° C. and 480° C., preferably at a temperature between 300° C. and 450° C., and most preferably at a temperature between 330° C. and 400° C.

According to another embodiment of the present invention, the method further comprises step (f) of providing a solvent and contacting the at least one solid carrier provided in step (a) and/or the transition metal reagent provided in step (b) before or during step (c) in any order and preferably the solvent is a non-polar solvent, a polar solvent or a mixture thereof, more preferably the non-polar solvent is selected from the group consisting of pentane, cyclopentane, hexane, cyclohexane, benzene, toluene, 1,4-dioxane, chloroform, diethyl ether, dichloromethane and mixtures thereof and/or the polar solvent is selected from the group consisting of tetrahydrofuran, ethyl acetate, acetone, dimethylformamide, acetonitrile, dimethyl sulphoxide, nitromethane, propylene carbonate, formic acid, n-butanol, isopropanol, n-propanol, ethanol, methanol, acetic acid, water and mixtures thereof even more preferably the solvent is a polar solvent and most preferably the solvent is water.

According to another embodiment of the present invention, the method further comprises step (g) of removing at least part of the solvent after step (c) and before step (d) by evaporation and/or filtration and/or centrifugation and/or spray drying to obtain a concentrated mixture.

According to another embodiment of the present invention, the method further comprises step (h) of thermally treating the mixture of step (c) or the concentrated mixture of step (g) at a temperature between 25° C. and 200° C., preferably at a temperature between 50° C. and 180° C., and most preferably at a temperature between 100° C. to 150° C.

According to another embodiment of the present invention, the transition metal reagent is selected from the group consisting of (NH4)2Ni(SO4)2, Ni(OCOCH3)2, NiBr2, NiCl2, NiF2, Ni(OH)2, NiI2, Ni(NO3)2, Ni(ClO4)2, Ni(SO3NH2)2, NiSO4, K2Ni(H2IO6)2, K2Ni(CN)4, [Ru(NH3)6]Cl2, [Ru(NH3)6]Cl3, [Ru(NH3)5Cl]Cl2, RuCl3, RuI3, RuF5, Ru(NO)(NO3)3, HAuCl4, AuBr3, AuCl, AuCl3, Au(OH)3, AuI, KAuCl4, Cu2S, copper(I)-thiophene-2-carboxylate, CuBr, CuCN, CuCl, CuF, CuI, CuH, CuSCN, CuBr2, CuCO3, CuCl2, CuF2, Cu(NO3)2, Cu3(PO4)2, Cu(OH)2, CuI2, CuS, CuSO4, Cu2(OAc)4, (NH4)2Fe(SO4)2, FeBr2, FeBr3, FeCl2, FeCl3, FeF2, FeF3, FeI2, Fe(NO3)3, FeC2O4, Fe2(C2O4)3, Fe(ClO4)2, FePO4, FeSO4, Fe(BF4)2, K4Fe(CN)6 and mixtures thereof, preferably is selected from the group consisting of (NH4)2Ni(SO4)2, Ni(OCOCH3)2, NiBr2, NiCl2, NiF2, Ni(OH)2, NiI2, Ni(NO3)2, Ni(ClO4)2, Ni(SO3NH2)2, NiSO4, K2Ni(H2IO6)2, K2Ni(CN)4, [Ru(NH3)6]Cl2, [Ru(NH3)6]Cl3, [Ru(NH3)5Cl]Cl2, RuCl3, RuI3, RuF5, Ru(NO)(NO3)3, HAuCl4, AuBr3, AuCl, AuCl3, Au(OH)3, AuI, KAuCl4, Cu2S, copper(I)-thiophene-2-carboxylate, CuBr, CuCN, CuCl, CuF, CuI, CuH, CuSCN, CuBr2, CuCO3, CuCl2, CuF2, Cu(NO3)2, Cu3(PO4)2, Cu(OH)2, CuI2, CuS, CuSO4, Cu2(OAc)4, and mixtures thereof, more preferably is selected from (NH4)2Ni(SO4)2, Ni(OCOCH3)2, NiBr2, NiCl2, NiF2, Ni(OH)2, NiI2, Ni(NO3)2, Ni(ClO4)2, Ni(SO3NH2)2, NiSO4, K2Ni(H2IO6)2, K2Ni(CN)4, [Ru(NH3)6]Cl2, [Ru(NH3)6]Cl3, [Ru(NH3)5Cl]Cl2, RuCl3, RuI3, RuF5, Ru(NO)(NO3)3, HAuCl4, AuBr3, AuCl, AuCl3, Au(OH)3, AuI, KAuCl4, and most preferably is selected from Ni(NO3)2, RuNO(NO3) and HAuCl4.

According to another embodiment of the present invention, the process further comprises step (D) of recovering and optionally recycling the catalytic system following the chemical reaction of step (C).

Method for Manufacturing the Catalytic System

As set out hereinabove, the method for manufacturing the inventive catalytic system comprising a transition metal compound on a solid carrier comprises steps (a)-(d). Said process optionally further comprises steps (e) and/or (f) and/or (g) and/or (h).

It should be understood, that the method of the present invention may be carried out as a continuous process or as a batch process. Preferably, the inventive method is carried out as a batch process.

In the following, it is referred to further details of the present invention and especially to the foregoing steps of the inventive process for locating the transition metal on the surface of a ground natural calcium carbonate and/or precipitated calcium carbonate.

It should be known that the defined embodiments of the inventive method also apply to the inventive catalytic system, as well as to the use of the inventive catalytic system, to the use of a solid carrier loaded with a transition metal as a catalyst and to the inventive products in different shapes such as granules, mouldings or extrudates and vice versa.

Step (a): Providing at Least One Solid Carrier

According to step a) of the present invention, at least one solid carrier is provided. The solid carrier is ground natural calcium carbonate (GNCC) and/or precipitated calcium carbonate (PCC) and has a specific surface area of from 3 to 50 m²/g measured using nitrogen and the BET method according to ISO 9277:2010.

The at least one solid carrier is not a surface-reacted calcium carbonate (SRCC). A surface-reacted calcium carbonate is a reaction product of natural ground calcium carbonate or precipitated calcium carbonate with carbon dioxide and one or more H3O+ ion donors, wherein the carbon dioxide is formed in situ by the H3O+ ion donors treatment and/or is supplied from an external source.

The expression "at least one" solid carrier means that one or more, for example, two or three solid carriers may be provided. According to a preferred embodiment, the at least one solid carrier comprises only one solid carrier as provided in step a).

According to a preferred embodiment of the present invention the at least one solid carrier material is selected from the group consisting of ground natural calcium carbonate (GNCC), preferably marble, limestone, dolomite and/or chalk, precipitated calcium carbonate (PCC), preferably vaterite, calcite and/or aragonite, more preferably the at least one calcium carbonate-containing filler material is precipitated calcium carbonate.

Natural or ground calcium carbonate (GCC) is understood to be manufactured from a naturally occurring form of calcium carbonate, mined from sedimentary rocks such as limestone or chalk, or from metamorphic marble rocks, eggshells or seashells. Calcium carbonate is known to exist as three types of crystal polymorphs: calcite, aragonite and vaterite. Calcite, the most common crystal polymorph, is considered to be the most stable crystal form of calcium carbonate. Less common is aragonite, which has a discrete or clustered needle orthorhombic crystal structure. Vaterite is the rarest calcium carbonate polymorph and is generally unstable. Ground calcium carbonate is almost exclusively of the calcitic polymorph, which is said to be trigonal-rhombohedral and represents the most stable form of the calcium carbonate polymorphs. The term "source" of the calcium carbonate in the meaning of the present application refers to the naturally occurring mineral material from which the calcium carbonate is obtained. The source of the calcium carbonate may comprise further naturally occurring components such as magnesium carbonate, alumino silicate etc.

In general, the grinding of natural ground calcium carbonate may be a dry or wet grinding step and may be carried out with any conventional grinding device, for example, under conditions such that comminution predominantly results from impacts with a secondary body, i.e. in one or more of: a ball mill, a rod mill, a vibrating mill, a roll crusher, a centrifugal impact mill, a vertical bead mill, an attrition mill, a pin mill, a hammer mill, a pulveriser, a shredder, a de-clumper, a knife cutter, or other such equipment known to the skilled man. In case the calcium carbonate-comprising mineral material comprises a wet ground calcium carbonate-comprising mineral material, the grinding step may be performed under conditions such that autogenous grinding takes place and/or by horizontal ball milling, and/or other such processes known to the skilled man. The wet processed ground calcium carbonate-comprising mineral material thus obtained may be washed and dewatered by well-known processes, e.g. by flocculation, filtration or forced evaporation prior to drying. The subsequent step of drying (if necessary) may be carried out in a single step such as spray drying, or in at least two steps. It is also common that such a mineral material undergoes a beneficiation step (such as a flotation, bleaching or magnetic separation step) to remove impurities.

According to one embodiment of the present invention the source of natural or ground calcium carbonate (GCC) is selected from marble, chalk, limestone, dolomite or mixtures thereof. Preferably, the source of ground calcium carbonate is marble, and more preferably dolomitic marble and/or magnesitic marble. According to one embodiment of the present invention the GCC is obtained by dry grinding. According to another embodiment of the present invention the GCC is obtained by wet grinding and subsequent drying.

"Dolomite" in the meaning of the present invention is a calcium carbonate-comprising mineral, namely a carbonic calcium-magnesium-mineral, having the chemical composition of $CaMg(CO_3)_2$ ("$CaCO_3 \cdot MgCO_3$"). A dolomite mineral may contain at least 30.0 wt.-% $MgCO_3$, based on the total weight of dolomite, preferably more than 35.0 wt.-%, and more preferably more than 40.0 wt.-% $MgCO_3$.

According to one embodiment of the present invention, the at least one solid carrier comprises one type of ground calcium carbonate. According to another embodiment of the present invention, the at least one solid carrier comprises a mixture of two or more types of ground calcium carbonates selected from different sources.

"Precipitated calcium carbonate" (PCC) in the meaning of the present invention is a synthesized material, generally obtained by precipitation following reaction of carbon dioxide and lime in an aqueous environment or by precipitation of a calcium and carbonate ion source in water or by precipitation by combining calcium and carbonate ions, for example $CaCl_2$ and $Na_2CO_3$, out of solution. Further possible ways of producing PCC are the lime soda process, or the Solvay process in which PCC is a by-product of ammonia production. Precipitated calcium carbonate exists in three primary crystalline forms: calcite, aragonite and vaterite, and there are many different polymorphs (crystal habits) for each of these crystalline forms. Calcite has a trigonal structure with typical crystal habits such as scalenohedral (S-PCC), rhombohedral (R-PCC), hexagonal prismatic, pinacoidal, colloidal (C-PCC), cubic, and prismatic (P-PCC). Aragonite is an orthorhombic structure with typical crystal habits of twinned hexagonal prismatic crystals, as well as a diverse assortment of thin elongated prismatic, curved bladed, steep pyramidal, chisel shaped crystals, branching tree, and coral or worm-like form. Vaterite belongs to the hexagonal crystal system. The obtained PCC slurry can be mechanically dewatered and dried.

According to one embodiment of the present invention, the at least one solid carrier is precipitated calcium carbonate, preferably comprising aragonitic, vateritic or calcitic mineralogical crystal forms or mixtures thereof.

According to one embodiment of the present invention, the at least one solid carrier comprises one type of precipitated calcium carbonate. According to another embodiment of the present invention, the at least one solid carrier comprises a mixture of two or more precipitated calcium carbonates selected from different crystalline forms and different polymorphs of precipitated calcium carbonate. For example, the at least one precipitated calcium carbonate may comprise one PCC selected from S-PCC and one PCC selected from R-PCC.

It is appreciated that the amount of calcium carbonate in the at least one solid carrier is at least 80 wt.-%, e.g. at least 95 wt.-%, preferably between 97 and 100 wt.-%, more preferably between 98.5 and 99.95 wt.-%, based on the total dry weight of the at least one solid carrier.

The at least one solid carrier is preferably in the form of a particulate material, and may have a particle size distribution as conventionally employed for the material(s) involved in the type of product to be produced. In general, it is preferred that the at least one solid carrier has a weight median particle size d50 value in the range from 1 to 75 μm.

For example, the at least one solid carrier has a weight median particle size d50 from 2 μm to 50 μm, more preferably from 3 to 40 μm even more preferably from 4 to 30 μm and most preferably from 5 μm to 15 μm.

Additionally or alternatively, the at least one solid carrier has a top cut (d98) in the range of 2 to 150 μm, preferably from 6 to 80 μm, even more preferably from 8 to 60 μm and most preferably from 10 to 30 μm.

The at least one solid carrier has a BET specific surface area of from 3 and 50 m2/g as measured by the BET nitrogen method. According to a preferred embodiment, the at least one solid carrier has a specific surface area (BET) of from 5 to 40 m2/g, more preferably of from 7 to 35 m2/g and most preferably of from 10 to 30 m2/g as measured by the BET nitrogen method.

Additionally or alternatively, the at least one solid carrier has a residual total moisture content of from 0.01 to 1 wt.-%, preferably from 0.01 to 0.2 wt.-%, more preferably from 0.02 to 0.2 wt.-% and most preferably from 0.03 to 0.2 wt.-%, based on the total dry weight of the at least one solid carrier.

Thus it is preferred that the at least one solid carrier has:
(i) a specific surface area in the range of from 5 to 40 $m^2/g$, preferably from 7 to 35 $m^2/g$ and more preferably from 10 to 30 $m^2/g$, measured using nitrogen and the BET method according to ISO 9277:2010; and/or
(ii) a $d_{50}(wt)$ in the range of from 1 to 75 μm, preferably from 2 to 50 μm, more preferably from 3 to 40 μm, even more preferably from 4 to 30 μm and most preferably from 5 to 15 μm; and/or
(iii) a $d_{98}(wt)$ in the range of from 2 to 150 μm, preferably from 4 to 100 μm, more preferably from 6 to 80 μm, even more preferably from 8 to 60 μm and most preferably from 10 to 30 μm.

For example, the at least one solid carrier has:
(i) a specific surface area in the range of from 5 to 40 $m^2/g$, preferably from 7 to 35 $m^2/g$ and more preferably from 10 to 30 $m^2/g$, measured using nitrogen and the BET method according to ISO 9277:2010; or
(ii) a $d_{50}(wt)$ in the range of from 1 to 75 μm, preferably from 2 to 50 μm, more preferably from 3 to 40 μm, even more preferably from 4 to 30 μm and most preferably from 5 to 15 μm; or
(iii) a $d_{98}(wt)$ in the range of from 2 to 150 μm, preferably from 4 to 100 μm, more preferably from 6 to 80 μm, even more preferably from 8 to 60 μm and most preferably from 10 to 30 μm.

Alternatively, the at least one solid carrier has:
(i) a specific surface area in the range of from 5 to 40 $m^2/g$, preferably from 7 to 35 $m^2/g$ and more preferably from 10 to 30 $m^2/g$, measured using nitrogen and the BET method according to ISO 9277:2010; and
(ii) a $d_{50}(wt)$ in the range of from 1 to 75 μm, preferably from 2 to 50 μm, more preferably from 3 to 40 μm, even more preferably from 4 to 30 μm and most preferably from 5 to 15 μm; and
(iii) a $d_{98}(wt)$ in the range of from 2 to 150 μm, preferably from 4 to 100 μm, more preferably from 6 to 80 μm, even more preferably from 8 to 60 μm and most preferably from 10 to 30 μm.

According to a preferred embodiment of the present invention, the at least one solid carrier is a precipitated calcium carbonate and has
(i) a specific surface area in the range of from 10 to 30 $m^2/g$, measured using nitrogen and the BET method according to ISO 9277:2010, preferably about 12 $m^2/g$; and (ii) a $d_{50}$(wt) in the range of from 1 to 75 µm, preferably about 1.5 µm; and
(iii) a $d_{98}$(wt) in the range of from 6 to 80 µm, preferably about 6.2 µm.

For the purpose of step (a) of the present invention, the solid carrier may be provided either in dried form or as a suspension in a suitable liquid medium. Unless specified otherwise, the terms "dried" or "dry" refer to a material having constant weight at 200° C., whereby constant weight means a change of 1 mg or less over a period of 30 s per 5 g of sample.

In a preferred embodiment, the solid carrier is provided in dried form.

Step (b): Providing at Least One Transition Metal Reagent

In step (b) of the manufacturing method according to the present invention, at least one transition metal reagent is provided.

The transition metal reagent according to the present invention comprises Ni ions, Ru ions, Au ions, Fe ions, Cu ions and mixtures thereof and is provided in such an amount that the amount of said ions is from 0.1 to 30 wt.-%, based on the dry weight of the solid carrier. It is preferred that the transition metal in the transition metal reagent shows catalytic activity and good selectivity in chemical reactions.

In principle, there exist four types of reagents, depending on how the constituent atoms are held together: molecules held together by covalent bonds, salts held together by ionic bonds, intermetallic compounds held together by metallic bonds, and certain complexes held together by coordinate covalent bonds. The transition metal reagent thus may be a molecular transition metal reagent, a transition metal salt, a metallic transition metal compound including the elemental transition metal or a transition metal complex.

According to a preferred embodiment of the present invention, the transition metal reagent is a transition metal salt or a transition metal complex.

In another preferred embodiment according to the present invention, the transition metal reagent comprises one or more of the following counter ions: hydride, oxide, hydroxide, sulphide, fluoride, chloride, bromide, iodide, carbonate, acetate, cyanide, thiocyanate, nitrate, nitrosyl nitrate, phosphate and sulphate.

In another preferred embodiment, the transition metal reagent comprises one or more of the following ligands: acetylacetonate (acac), chloride, acetate, triphenylphosphine, 1,1'-bis(diphenylphosphino)ferrocene (dppf), 1,2-bis (diphenyl-phosphino)ethane (dppe), 1,3-bis(diphenylphosphino)propane (dppp), 1,4-bis(diphenyl-phosphino)butane (dppb), allyl, dibenzylidene acetone or dibenzalacetone (dba), and ethylenediamine.

In a preferred embodiment, the transition metal is selected from Ni, Ru, Au, Fe, Cu and mixtures thereof, preferably Ni, Ru, Au Cu and mixtures thereof, more preferably Ni, Ru, Au and mixtures thereof and most preferably is Ru and the transition metal reagent is a transition metal salt or a transition metal complex. In a further preferred embodiment, the foregoing transition metal salt comprises one or more of the following counter ions: hydride, oxide, hydroxide, sulphide, fluoride, chloride, bromide, iodide, carbonate, acetate, cyanide, thiocyanate, nitrate, nitrosyl nitrate, phosphate and sulphate and/or the foregoing transition metal complex comprises one or more of the following ligands: acac, chloride, acetate, triphenylphosphine, dppf, dppe, dppp, dppb, allyl, dba and ethylenediamine.

According to a preferred embodiment the transition metal salt and/or the transition metal complex is water soluble and, therefore, forms a solution when dissolved in water. The "absolute water solubility" of a compound is to be understood as the maximum concentration of a compound in water where one can observe a single phase mixture at 20° C. under equilibrium conditions. The absolute water solubility is given in g compound per 100 g water. According to a preferred embodiment the transition metal salt and/or the transition metal complexes have absolute water solubilities of above 0.1 g per 100 g water, preferably of above 1 g per 100 g water and most preferably of above 5 g per 100 g water.

According to another embodiment, the transition metal reagent is selected from the group consisting of (NH4)2Ni (SO4)2, Ni(OCOCH3)2, NiBr2, NiCl2, NiF2, Ni(OH)2, NiI2, Ni(NO3)2, Ni(ClO4)2, Ni(SO3NH2)2, NiSO4, K2Ni (H2IO6)2, K2Ni(CN)4, [Ru(NH3)6]Cl2, [Ru(NH3)6]Cl3, [Ru(NH3)5Cl]Cl2, RuCl3, RuI3, RuF5, Ru(NO)(NO3)3, HAuCl4, AuBr3, AuCl, AuCl3, Au(OH)3, AuI, KAuCl4, Cu2S, copper(I)-thiophene-2-carboxylate, CuBr, CuCN, CuCl, CuF, CuI, CuH, CuSCN, CuBr2, CuCO3, CuCl2, CuF2, Cu(NO3)2, Cu3(PO4)2, Cu(OH)2, CuI2, CuS, CuSO4, Cu2(OAc)4, (NH4)2Fe(SO4)2, FeBr2, FeBr3, FeCl2, FeCl3, FeF2, FeF3, FeI2, Fe(NO3)3, FeC2O4, Fe2 (C2O4)3, Fe(ClO4)2, FePO4, FeSO4, Fe(BF4)2, K4Fe (CN)6 and mixtures thereof, preferably is selected from the group consisting of (NH4)2Ni(SO4)2, Ni(OCOCH3)2, NiBr2, NiCl2, NiF2, Ni(OH)2, NiI2, Ni(NO3)2, Ni(ClO4)2, Ni(SO3NH2)2, NiSO4, K2Ni(H2IO6)2, K2Ni(CN)4, [Ru (NH3)6]Cl2, [Ru(NH3)6]Cl3, [Ru(NH3)5Cl]Cl2, RuCl3, RuI3, RuF5, Ru(NO)(NO3)3, HAuCl4, AuBr3, AuCl, AuCl3, Au(OH)3, AuI, KAuCl4, Cu2S, copper(I)-thiophene-2-carboxylate, CuBr, CuCN, CuCl, CuF, CuI, CuH, CuSCN, CuBr2, CuCO3, CuCl2, CuF2, Cu(NO3)2, Cu3 (PO4)2, Cu(OH)2, CuI2, CuS, CuSO4, Cu2(OAc)4 and mixtures thereof, more preferably is selected from (NH4) 2Ni(SO4)2, Ni(OCOCH3)2, NiBr2, NiCl2, NiF2, Ni(OH)2, NiI2, Ni(NO3)2, Ni(ClO4)2, Ni(SO3NH2)2, NiSO4, K2Ni (H2IO6)2, K2Ni(CN)4, [Ru(NH3)6]Cl2, [Ru(NH3)6]Cl3, [Ru(NH3)5Cl]Cl2, RuCl3, RuI3, RuF5, Ru(NO)(NO3)3, HAuCl4, AuBr3, AuCl, AuCl3, Au(OH)3, AuI, KAuCl4 and mixtures thereof, and most preferably is selected from Ni(NO3)2, RuNO(NO3) and HAuCl4.

For the purpose of step (b), the transition metal reagent may in principle be provided in any form, meaning that the transition metal compound may be provided as a neat compound or it may be provided in a liquid medium in form of a solution or suspension.

The transition metal reagent according to the present invention is provided in such an amount that the amount of said ions is from 0.1 to 30 wt.-%, based on the dry weight of the solid carrier. Alternatively, the transition metal reagent according to the present invention is provided in such an amount that the amount of said ions is from 0.25 to 25 wt. %, preferably from 0.5 to 20 wt. %, more preferably 1 to 15 wt. %, even more preferably from 2 to 10 wt. % and most preferably from 2.5 to 5 wt. %, based on the dry weight of the solid carrier.

In case the transition metal is Cu, the transition metal reagent according to the present invention is preferably provided in such an amount that the amount of said ion is from above 3.0 to 30 wt.-%, based on the dry weight of the solid carrier. Alternatively, the transition metal reagent according to the present invention is provided in such an amount that the amount of said ion is from 3.25 to 25 wt. %, preferably from 3.5 to 20 wt. %, more preferably 4 to 15 wt. %, even more preferably from 4.25 to 10 wt. % and most preferably from 4.5 to 5 wt. %, based on the dry weight of the solid carrier.

Optional Step (f): Providing a Solvent

According to one embodiment of the present invention, the method further comprises optional step (f) of providing a solvent and contacting the at least one solid carrier provided in step (a) and/or the transition metal reagent provided in step (b) before or during step (c) in any order.

According to one embodiment of the present invention only the at least one solid carrier provided in step (a) is contacted with the solvent. Said slurry may have a solid content within the range of from 1 to 95 wt.-%, preferably from 3 to 60 wt.-%, more preferably from 5 to 40 wt.-% and most preferably from 10 to 25 wt.-%, based on the total weight of the slurry. To the obtained slurry the at least one transition metal reagent is added in dry form.

Alternatively, the at least one transition metal reagent provided in step (b) is contacted with the solvent. Said slurry or solution may have a solids content within the range of from 0.1 to 50 wt.-%, preferably from 0.1 to 40 wt.-%, more preferably from 0.2 to 3 wt.-% and most preferably from 0.5 to 10 wt.-%, based on the total weight of the slurry or solution. To the obtained slurry or solution the at least one solid carrier is added in dry form.

The contacting of the at least one transition metal reagent provided in step (b) with a solvent in step (f) may be preferred as this may lead to a more homogenous mixture in any of the subsequent steps, for example in contacting step (c) of the inventive method for manufacturing the catalytic system. For the same reason, solutions may be preferred over suspensions. In a preferred embodiment, the transition metal reagent provided in step (b) is thus in form of a solution or suspension in step (c), preferably in form of a solution.

According to a preferred embodiment two solvents are provided. The at least one solid carrier provided in step (a) is contacted with one solvent and the at least one transition metal reagent provided in step (b) is contacted with the other solvent. Afterwards both slurries or the slurry and the solution are mixed.

The solvent for the provision of the at least one solid carrier and the solvent for the provision of the at least one transition metal reagent may be the same or may be different. According to a preferred embodiment the two solvents are the same.

According to one embodiment the solvent is a non-polar solvent, a polar solvent or a mixture thereof.

According to a preferred embodiment of the present invention, the non-polar solvent is selected from the group consisting of pentane, cyclopentane, hexane, cyclohexane, benzene, toluene, 1,4-dioxane, chloroform, diethyl ether, dichloromethane and mixtures thereof. According to another preferred embodiment of the present invention, the polar solvent is selected from the group consisting of tetrahydrofuran, ethyl acetate, acetone, dimethylformamide, acetonitrile, dimethyl sulphoxide, nitromethane, propylene carbonate, formic acid, n-butanol, isopropanol, n-propanol, ethanol, methanol, acetic acid, water and mixtures thereof.

According to another preferred embodiment of the present invention, the solvent for the solid carrier and/or the transition metal reagent is a polar solvent and most preferably is water.

Step (c): Contacting the at Least One Solid Carrier and the Transition Metal Reagent In step (c) of the manufacturing method according to the present invention, the at least one solid carrier provided in step (a) and the at least one transition metal reagent provided in step (b) are brought into contact to obtain a mixture comprising a solid carrier and a transition metal reagent.

Step (c) of contacting the solid carrier and the transition metal reagent serves to impregnate at least part of the accessible surface of the solid carrier with said transition metal reagent.

The contacting of the at least one solid carrier provided in step (a) and the at least one transition metal reagent provided in step (b) can be accomplished by any conventional means known to the skilled person.

According to one embodiment of the present invention, step (c) comprises the steps of providing the at least one solid carrier provided in step (a) in a first step and then adding the at least one transition metal reagent provided in step (b) in a subsequent step. According to another embodiment of the present invention, step (c) comprises the steps of first providing the at least one transition metal reagent provided in step (b) and subsequently adding the at least one solid carrier provided in step (a). According to still another embodiment, the at least one solid carrier provided in step (a) and the at least one transition metal reagent provided in step (b) are provided and contacted simultaneously.

In case the at least one solid carrier provided in step (a) is provided as a first step, it is possible to add the at least one transition metal reagent provided in step (b) in one portion or it may be added in several equal or unequal portions, i.e. in larger and smaller portions.

During contacting step (c) of the inventive process, a mixture comprising the solid carrier of step (a) and the transition metal reagent of step (b) is obtained. Said mixture may be a solid, preferably in powder form or a suspension or slurry in liquid form. Preferably the mixture is a suspension or slurry in liquid form.

In one embodiment of the method according to the present invention (i) the at least one solid carrier of step (a) is provided in a solvent in form of a suspension; and/or (ii) the at least one transition metal reagent of step (b) is provided in a solvent in form of a solution or a suspension, preferably in form of a solution.

In a preferred embodiment, the solid carrier is provided as a suspension in a solvent, wherein also the transition metal reagent is provided in a solvent in form of a solution or suspension, preferably in form of a solution.

As already described hereinabove, the solid carrier may be provided as a suspension or slurry, in which case the suspension or slurry will contain a suitable solvent. In general, said solvent may differ from the solvent described herein as a suitable solvent for the provision of the at least one transition metal reagent in form of a solution or a suspension.

However, in a preferred embodiment, the solvent for the provision of the at least one solid carrier and the solvent for the provision of the at least one transition metal reagent is the same.

The mixture obtained in step (c) may comprise any of the solvent(s) disclosed hereinabove, for example the solvent(s) may be a non-polar solvent, a polar solvent or a mixture thereof, preferably the non-polar solvent is selected from the group consisting of pentane, cyclopentane, hexane, cyclohexane, benzene, toluene, 1,4-dioxane, chloroform, diethyl ether, dichloromethane and mixtures thereof and/or the polar solvent is selected from the group consisting of tetrahydrofuran, ethyl acetate, acetone, dimethylformamide, acetonitrile, dimethyl sulphoxide, nitromethane, propylene carbonate, formic acid, n-butanol, isopropanol, n-propanol, ethanol, methanol, acetic acid, water and mixtures thereof. Preferably, the mixture obtained in step (c) further comprises water, ethanol, ethanol/water mixtures, toluene and mixtures thereof and most preferably further comprises water.

The contacting step (c) can be carried out by any means known in the art. For example, the at least one solid carrier of step (a) and the transition metal reagent of step (b) can be brought into contact by spraying and/or mixing. Suitable devices for spraying or mixing are known to the skilled person.

According to one embodiment of the present invention, step (c) may be carried out by spraying. Preferably, step (c) is carried out by mixing.

The mixing in step (c) can be accomplished by any conventional means known to the skilled person. The skilled person will adapt the mixing conditions such as the mixing speed, dividing, and temperature according to his process equipment. Additionally, the mixing may be carried out under homogenising and/or particle dividing conditions.

For example, mixing and homogenising may be performed by use of a ploughshare mixer. Ploughshare mixers function by the principle of a fluidised bed which is produced mechanically. Ploughshare blades rotate close to the inside wall of a horizontal cylindrical drum, thereby conveying the components of the mixture out of the product bed and into the open mixing space. Said fluidised bed ensures intense mixing of even large batches in a very short time. Choppers and/or dispersers are used to disperse lumps in case of a dry operating mode. Equipment that may be used in the inventive process is commercially available, for example, from Gebrüder Lödige Maschinenbau GmbH, Germany or from VISCO JET Rührsysteme GmbH, Germany.

According to another embodiment of the present invention, step (c) is carried out for at least 1 second, preferably for at least 1 minute (e.g. 10 min, 30 min or 60 min). According to a preferred embodiment step (c) is carried out for a period of time ranging from 1 second to 60 min, preferably for a period of time ranging from 15 min to 45 min. For example, mixing step (d) is carried out for 30 min±5 min.

It is also within the confines of the present invention that suitable solvent as described in optional step (f) may be added during process step (c), for example, in case the solid carrier is provided in dry form and the transition metal reagent is provided in neat form or in case it is intended to adjust the solids content or the Brookfield viscosity of the mixture to a specific value.

According to one embodiment of the present invention, the mixture obtained in step (c) has a solid content within the range of from 1 to 90 wt.-%, preferably from 3 to 60 wt.-%, more preferably from 5 to 40 wt.-% and most preferably from 10 to 25 wt.-%, based on the total weight of said mixture.

Optional Step (g): Removing at Least Part of the Solvent

The method according to the present invention may optionally comprise step (g) of removing at least part of the solvent after step (c) and before step (d) by evaporation and/or filtration and/or centrifugation and/or spray drying to obtain a concentrated mixture.

As already discussed hereinabove, the mixture obtained in contacting step (c) may comprise a solvent, for example if the at least one solid carrier in step (a) is provided as a suspension or slurry or if the at least one transition metal reagent in step (b) is provided in form of a solution or suspension.

Step (g) yields a concentrated mixture, which contains less solvent than the mixture obtained in contacting step (c). In principle, concentrating step (g) can be accomplished by any conventional means known to the skilled person, for example by evaporation of the liquid medium and/or by filtration and/or by centrifugation and/or by spray drying.

The method of choice in step (g) may depend on the nature of the solvent contained in the mixture of step (c). For example, it may be preferred to remove aprotic solvents (e.g. toluene) by evaporation while protic solvents (e.g. ethanol or water) may preferably be removed by filtration. In further instances, an initial filtration combined with subsequent evaporation of residual liquid medium under reduced pressure (vacuum) may be preferred.

According to one embodiment of the present invention, the inventive method further comprises step (g) of removing at least part of the solvent contained in the mixture of step (c) by evaporation. For example, evaporation of the solvent may be carried out by application of heat and/or reduced pressure using a vacuum pump.

According to another embodiment of the present invention, the inventive method further comprises step (g) of removing at least part of the solvent contained in the mixture of step (c) by filtration. For example, filtration may be carried out by means of a drum filter or a filter press or by means of nanofiltration.

According to still another embodiment of the present invention, the inventive method further comprises step (g) of removing at least part of the solvent contained in the mixture of step (c) by filtration and evaporation, preferably by filtration and subsequent evaporation.

According to still another embodiment of the present invention, the inventive method further comprises step (g) of removing at least part of the solvent contained in the mixture of step (c) by centrifugation. For example, centrifugation and decanting of the solvent may be carried out by a disc centrifuge.

According to still another embodiment of the present invention, the inventive method further comprises step (g) of removing at least part of the solvent contained in the mixture of step (c) by spray drying. For example, spray drying of the solvent may be carried out in a spray dryer.

The concentrated mixture obtained in step (g), after removing at least part of the solvent contained in the mixture of step (c), is a concentrated mixture. In a preferred embodiment, said concentrated mixture has a solids content of at least 70 wt.-%, preferably at least 80 wt.-%, more preferably at least 85 wt.-% and most preferably at least 90 wt.-%, based on the total weight of said mixture. For example, said concentrated mixture may have a solids content of 95 wt.-%, based on the total weight of said mixture.

According to still another embodiment of the inventive process, the solvent contained in the mixture of step (c) is removed in step (g) to obtain a dried mixture.

Optional Step (h): Thermal Treatment

According to optional step (h) of the method for manufacturing the inventive catalytic system, the mixture of step (c) or the concentrated mixture of optional step (g) is thermally treated at a temperature between 25° C. and 200° C., preferably at a temperature between 50° C. and 180° C., and most preferably at a temperature between 100 and 150° C.

The term "heating" or "thermally treatment" is not limiting the process according to the present invention to a process, wherein the temperature of the mixture is adjusted actively to the defined temperature range by addition of energy through an external heat source. Said term also comprises keeping the temperature reached in an exothermic reaction, for example in contacting step (c), during a specified period of time.

The thermal treatment may be carried out for a specific period of time. In one embodiment, step (h) is thus carried out for at least 5 mins, preferably for 0.25 h to 24 h, more preferably for 1 h to 5 h and most preferably for 2 to 3 h.

In a preferred embodiment, the mixture of step (c) or the concentrated mixture of optional step (g) is thermally treated at a temperature between 25° C. and 200° C., preferably at a temperature between 50° C. and 180° C., and most preferably at a temperature between 100 and 150° C., wherein said thermal treatment is carried out for at least 5 min, preferably for 0.25 h to 24 h, more preferably for 1 h to 5 h and most preferably for 2 to 3 h.

In general, the optional thermally treatment step may take place using any suitable thermally treatment/heating equipment and can, for example, include thermal heating and/or heating at reduced pressure using equipment such as an evaporator, a flash drier, an oven, a spray drier and/or drying in a vacuum chamber. The optional thermally treatment step can be carried out at reduced pressure, ambient pressure or under increased pressure. Preferably, the optional thermally heating step is performed at ambient pressure.

Step (d): Calcination Step

In step (d) the mixture of step (c) is calcined at a temperature between 250° C. and 500° C. By this calcination step the inventive catalytic system comprising a transition metal compound on the solid carrier is obtained, wherein the transition metal compound is selected from the group consisting of Ni oxides, Ru oxides, Au oxides, Fe oxides, Cu oxides and mixtures thereof, preferably is selected from the group consisting of Ni oxides, Ru oxides, Au oxides, Cu oxides and mixtures thereof, and most preferably is selected from the group consisting of Ni oxides, Ru oxides, Au oxides and mixtures thereof.

The term "calcination" according to the present invention denotes a thermal treatment at elevated temperatures leading to a partial or full thermal conversion of the transition metal reagent (partial of full calcination). During calcination the transition metal reagent comprising Ni ions, Ru ions, Au ions, Fe ions, Cu ions and mixtures thereof transforms partially or fully to Ni oxide, Ru oxide, Au oxide, Fe oxide, Cu oxide and combinations thereof. For example, the Ni ions, Ru ions, Au ions, Fe ions, Cu ions and mixtures thereof transform partially or fully to Ni oxide, Ru oxide, Au oxide, Fe oxide, Cu oxide and combinations thereof wherein the Ni in Ni oxide is in oxidation states Ni(I), Ni(II), Ni(III), Ni(IV), the Ru in Ru oxide is in oxidation states Ru(I), Ru(II), Ru(III), Ru(IV), Ru(V), Ru(VI), Ru(VII), Ru(VIII), the Au in Au oxide is in oxidation states Au(I), Au(II), Au(III), Au(V), the Fe in Fe oxide is in the oxidation states Fe(I), Fe(II), Fe(III), Fe(IV), Fe(V), Fe(VI), Fe(VII), the Cu in Cu oxide is in the oxidation states Cu(I), Cu(II), Cu(III), Cu(IV) and mixtures thereof. For example, the transition metal compound is selected from the group consisting of NiO, $Ni_2O_3$, $Ni_3O_4$, $RuO_2$, $Ru_2O_3$, $RuO_4$, $Au_2O$, $Au_2O_3$, FeO, $FeO_2$, $Fe_2O_3$, $Fe_3O_4$, CuO, $Cu_2O$, $CuO_2$, $Cu_2O_3$ and mixtures thereof, preferably is selected from the group consisting of NiO, $Ni_2O_3$, $Ni_3O_4$, $RuO_2$, $Ru_2O_3$, $RuO_4$, $Au_2O$, $Au_2O_3$, CuO, $Cu_2O$, $CuO_2$, $Cu_2O_3$ and mixtures thereof, more preferably is selected from the group consisting of NiO, $Ni_2O_3$, $Ni_3O_4$, $RuO_2$, $Ru_2O_3$, $RuO_4$, $Au_2O$, $Au_2O_3$ and mixtures thereof and most preferably is selected from the group consisting of $RuO_2$, $Ru_2O_3$, $RuO_4$ and mixtures thereof.

According to a preferred embodiment of the present invention, the calcination step (d) is performed at a temperature between 270° C. and 480° C., preferably at a temperature between 300° C. and 450° C., and most preferably at a temperature between 330° C. and 400° C.

The calcination step of the present invention is not limited to a step, wherein the temperature of the mixture is adjusted actively to the defined temperature range by addition of energy through an external heat source. The calcination step also comprises keeping the temperature reached in that step for a specified period of time.

The calcination step may be carried out for a specific period of time. In one embodiment, step (h) is thus carried out for at least 10 min, preferably for 0.5 h to 24 h, more preferably for 1 h to 5 h and most preferably for 2.5 to 3.5 h.

The calcination step may be carried out under air, N2 atmosphere, Ar atmosphere, O2 atmosphere or mixtures and preferably is carried out under air.

According to a preferred embodiment of the present invention, the calcination step is performed at a temperature between 250° C. and 500° C., preferably at a temperature between 270° C. and 480° C., more preferably at a temperature between 300° C. and 450° C., and most preferably at a temperature between 330° C. and 400° C., under air, N2 atmosphere, Ar atmosphere, 02 atmosphere or mixtures.

In general, the calcination step may take place using any suitable calcination/heating equipment and can, for example, include thermal heating and/or heating at reduced pressure using equipment such as a flash drier or an oven. Preferably, the calcination step is performed at ambient pressure.

According to a preferred embodiment of the present invention, the catalytic system merely consists of the at least one solid carrier and the transition metal compound on the surface of said carrier, wherein the transition metal compound is selected from the group consisting of Ni oxides, Ru oxides, Au oxides, Fe oxides, Cu oxides and mixtures thereof, preferably is selected from the group consisting of Ni oxides, Ru oxides, Au oxides, Cu oxides and mixtures thereof, and more preferably is selected from the group consisting of Ni oxides, Ru oxides, Au oxides and mixtures thereof.

After calcination the content of the transition metal species on the surface of the solid carrier is from 0.1 to 30 wt.-%, based on the dry weight of the solid carrier, preferably in the range of from 0.25 to 25 wt. %, more preferably from 0.5 to 20 wt. %, even more preferably 1 to 15 wt. %, even more preferably from 2 to 10 wt. % and most preferably from 2.5 to 5 wt. %, based on the dry weight of the solid carrier.

In addition to the Ni oxide, Ru oxide, Au oxide, Fe oxide, Cu oxide and mixtures thereof on the surface of the at least one solid carrier also other reaction compounds may be present after the calcination step. These reaction compounds may be products that are obtained from the counter ions of the transition metal salt or the ligands of the transition metal complex with calcium carbonate.

Preferably the amount of these reaction products is lower than 100 wt.-%, based on the dry weight of the transition metal species on the surface of the at least one solid carrier, more preferably lower than 80 wt.-%, even more preferably lower than 50 wt.-%, even more preferably lower than 30 wt.-% and most preferably lower than 10 wt.-% based on the dry weight of the transition metal species on the surface of the at least one solid carrier.

The inventors surprisingly found that by the above method it is possible to provide a catalytic system wherein the transition metal compound that is selected from the group consisting of Ni oxide, Ru oxide, Au oxide, Fe oxide, Cu oxide and combinations thereof is located on the solid carrier, which is a ground natural calcium carbonate and/or precipitated calcium carbonate. Furthermore, the above method is a cheap and simple production process, which provides the inventive catalytic system.

Optional Step (e): Reducing the Calcined Catalytic System

The calcined catalytic system obtained from step (d) can optionally be reduced in step (e). The reduction takes place under H2 atmosphere at a temperature between 100° C. and 500° C. By such a reduction step a catalytic system comprising a transition metal compound on the solid carrier is obtained, wherein the transition metal compound is selected from the group consisting of elemental Ni, elemental Ru, elemental Au, elemental Fe, elemental Cu and mixtures thereof, preferably is selected from the group consisting of elemental Ni, elemental Ru, elemental Au, elemental Cu and mixtures thereof, and even more preferably is selected from the group consisting of elemental Ni, elemental Ru, elemental Au, and mixtures thereof.

The term "reducing" in the meaning of the present invention refers to a chemical reaction wherein the oxidation state of the transition metal in in the transition metal reagent is changed from higher oxidation states to zero. More precisely, during reducing step (e) the transition metal reagent on the surface of the solid carrier undergoes a reaction wherein elemental Ni, elemental Ru, elemental Au, elemental Fe, elemental Cu and mixtures thereof are obtained on the surface of the at least one solid carrier.

For example, the transition metal reagent comprises the transition metal in an oxidation state of I to VIII and is reduced to an oxidation state of 0. More precisely, the transition metal reagent comprises Ni ions in oxidation states Ni(I), Ni(II), Ni(III), Ni(IV), Ru ions in oxidation states Ru(I), Ru(II), Ru(III), Ru(IV), Ru(V), Ru(VI), Ru(VII), Ru(VIII), Au ions in oxidation states Au(I), Au(II), Au(III), Au(V), Fe ions in the oxidation states Fe(I), Fe(II), Fe(III), Fe(IV), Fe(V), Fe(VI), Fe(VII), Cu ions in the oxidation states Cu(I), Cu(II), Cu(III), Cu(IV) and mixtures thereof and is reduced to elemental Ni having an oxidation state of Ni(0), elemental Ru having an oxidation state of Ru(0), elemental Au having an oxidation state of Au(0), elemental Fe having an oxidation state of Fe(0), elemental Cu having an oxidation state of Cu(0) and mixtures thereof.

In addition to the elemental Ni, elemental Ru, elemental Au, elemental Fe, elemental Cu and mixtures thereof on the surface of the at least one solid carrier also other reaction compounds may be present after the reduction step. These reaction compounds may be products that are obtained from the counter ions of the transition metal salt or the ligands of the transition metal complex with calcium carbonate.

Preferably the amount of these reaction products is lower than 100 wt.-%, based on the dry weight of the transition metal element on the surface of the at least one solid carrier, more preferably lower than 80 wt.-%, even more preferably lower than 50 wt.-%, even more preferably lower than 30 wt.-% and most preferably lower than 10 wt.-% based on the dry weight of the transition metal element on the surface of the at least one solid carrier.

According to a preferred embodiment of the present invention, the catalytic system merely consists of the at least one solid carrier and the transition metal compound on the surface of said carrier, wherein the transition metal compound is selected from the group consisting of elemental Ni, elemental Ru, elemental Au, elemental Fe, elemental Cu and mixtures thereof, preferably is selected from the group consisting of elemental Ni, elemental Ru, elemental Au, elemental Cu and mixtures thereof, even more preferably is selected from the group consisting of elemental Ni, elemental Ru, elemental Au, and mixtures thereof.

The reduction step (d) is performed under H2 atmosphere, which means that the H2 comprises from 5 vol.-% to 99.99 vol.-% of H2, based on the total volume of the gas, preferably from 7 vol.-% to 99.95 vol.-% of H2, even more preferably from 10 vol.-% to 99.90 vol.-% of H2 and most preferably from 15 to 99 vol.-% of H2, based on the total volume of the gas. The remaining gas up to 100 vol.-% is an inert gas such as nitrogen, argon and/or helium.

According to a preferred embodiment of the present invention, the reducing step (e) is performed at a temperature between 200° C. and 475° C., preferably at a temperature between 300° C. and 450° C., and most preferably at a temperature between 350° C. and 400° C.

The reducing step of the present invention is not limited to a step, wherein the temperature of the mixture is adjusted actively to the defined temperature range by addition of energy through an external heat source. The reducing step also comprises keeping the temperature reached in that step for a specified period of time.

The reducing step may be carried out for a specific period of time. In one embodiment, step (e) is thus carried out for at least 10 min, preferably for 0.5 h to 24 h, more preferably for 1 h to 5 h and most preferably for 2.5 to 3.5 h.

According to a preferred embodiment of the present invention, the reducing step (e) is performed at a temperature between 100 and 500° C., preferably between 200° C. and 475° C., more preferably at a temperature between 300° C. and 450° C., and most preferably at a temperature between 350° C. and 400° C. under H2 atmosphere for at least 10 min, preferably for 0.5 h to 24 h, more preferably for 1 h to 5 h and most preferably for 2.5 to 3.5 h.

After reduction the content of the transition metal species on the surface of the solid carrier is from 0.1 to 30 wt.-%, based on the dry weight of the solid carrier, preferably in the range of from 0.25 to 25 wt. %, more preferably from 0.5 to 20 wt. %, even more preferably 1 to 15 wt. %, even more preferably from 2 to 10 wt. % and most preferably from 2.5 to 5 wt. %, based on the dry weight of the solid carrier.

In case the transition metal is Cu, the content of the transition metal species on the surface of the solid carrier is from above 3.0 to 30 wt.-%, based on the dry weight of the solid carrier. Alternatively, the content of the transition metal species on the surface of the solid carrier is from 3.25 to 25 wt. %, preferably from 3.5 to 20 wt. %, more preferably 4 to 15 wt. %, even more preferably from 4.25 to 10 wt. % and most preferably from 4.5 to 5 wt. %, based on the dry weight of the solid carrier.

The inventors surprisingly found that by the above method it is possible to provide a catalytic system wherein the transition metal compound that is selected from the group consisting of elemental Ni, elemental Ru, elemental Au, elemental Fe, elemental Cu and mixtures thereof is located on the solid carrier, which is a ground natural calcium carbonate and/or precipitated calcium carbonate. Furthermore, the above method is a cheap and simple production process, which provides the inventive catalytic system.

As already set out above the inventive method for manufacturing the catalytic system comprising the transition metal compound on a solid carrier comprises the steps of:
(a) providing at least one solid carrier, wherein the solid carrier is ground natural calcium carbonate (GNCC) and/or precipitated calcium carbonate (PCC) and has a specific surface area of from 3 to 50 m$^2$/g measured using nitrogen and the BET method according to ISO 9277:2010;

(b) providing at least one transition metal reagent comprising Ni ions, Ru ions, Au ions, Fe ions, Cu ions and mixtures thereof, in such an amount that the amount of said ions is from 0.1 to 30 wt.-%, based on the dry weight of the solid carrier;
(c) contacting the at least one solid carrier provided in step (a) and the transition metal reagent provided in step (b) to obtain a mixture comprising a solid carrier and a transition metal reagent; and
(d) calcining the mixture of step (c) at a temperature between 250° C. and 500° C. for obtaining a catalytic system comprising a transition metal compound on the solid carrier, wherein the transition metal compound is selected from the group consisting of Ni oxides, Ru oxides, Au oxides, Fe oxides, Cu oxides and mixtures thereof.

According to another embodiment of the present invention the method for manufacturing the catalytic system comprising the transition metal compound on a solid carrier comprises the steps of:
(a) providing at least one solid carrier, wherein the solid carrier is ground natural calcium carbonate (GNCC) and/or precipitated calcium carbonate (PCC) and has a specific surface area of from 3 to 50 $m^2/g$ measured using nitrogen and the BET method according to ISO 9277:2010;
(b) providing at least one transition metal reagent comprising Ni ions, Ru ions, Au ions, Fe ions, Cu ions and mixtures thereof, in such an amount that the amount of said ions is from 0.1 to 30 wt.-%, based on the dry weight of the solid carrier;
(c) contacting the at least one solid carrier provided in step (a) and the transition metal reagent provided in step (b) to obtain a mixture comprising a solid carrier and a transition metal reagent;
(d) calcining the mixture of step (c) at a temperature between 250° C. and 500° C. for obtaining a catalytic system comprising a transition metal compound on the solid carrier, wherein the transition metal compound is selected from the group consisting of Ni oxides, Ru oxides, Au oxides, Fe oxides, Cu oxides and mixtures thereof; and
(e) reducing the calcined catalytic system obtained from step (d) under $H_2$ atmosphere at a temperature between 100° C. and 500° C. for obtaining a catalytic system comprising a transition metal compound on the solid carrier, wherein the transition metal compound is selected from the group consisting of elemental Ni, elemental Ru, elemental Au, elemental Fe, elemental Cu and mixtures thereof.

According to another embodiment of the present invention the method for manufacturing the catalytic system comprising the transition metal compound on a solid carrier comprises the steps of:
(a) providing at least one solid carrier, wherein the solid carrier is ground natural calcium carbonate (GNCC) and/or precipitated calcium carbonate (PCC) and has a specific surface area of from 3 to 50 $m^2/g$ measured using nitrogen and the BET method according to ISO 9277:2010;
(b) providing at least one transition metal reagent comprising Ni ions, Ru ions, Au ions, Fe ions, Cu ions and mixtures thereof, in such an amount that the amount of said ions is from 0.1 to 30 wt.-%, based on the dry weight of the solid carrier;
(c) contacting the at least one solid carrier provided in step (a) and the transition metal reagent provided in step (b) to obtain a mixture comprising a solid carrier and a transition metal reagent;
(d) calcining the mixture of step (c) at a temperature between 250° C. and 500° C. for obtaining a catalytic system comprising a transition metal compound on the solid carrier, wherein the transition metal compound is selected from the group consisting of Ni oxides, Ru oxides, Au oxides, Fe oxides, Cu oxides and mixtures thereof; and
(e) optionally reducing the calcined catalytic system obtained from step (d) under $H_2$ atmosphere at a temperature between 100° C. and 500° C. for obtaining a catalytic system comprising a transition metal compound on the solid carrier, wherein the transition metal compound is selected from the group consisting of elemental Ni, elemental Ru, elemental Au, elemental Fe, elemental Cu and mixtures thereof; and
(f) providing a solvent and contacting the at least one solid carrier provided in step (a) and/or the transition metal reagent provided in step (b) before or during step (c) in any order.

According to another embodiment of the present invention the method for manufacturing the catalytic system comprising the transition metal compound on a solid carrier comprises the steps of:
(a) providing at least one solid carrier, wherein the solid carrier is ground natural calcium carbonate (GNCC) and/or precipitated calcium carbonate (PCC) and has a specific surface area of from 3 to 50 $m^2/g$ measured using nitrogen and the BET method according to ISO 9277:2010;
(b) providing at least one transition metal reagent comprising Ni ions, Ru ions, Au ions, Fe ions, Cu ions and mixtures thereof, in such an amount that the amount of said ions is from 0.1 to 30 wt.-%, based on the dry weight of the solid carrier;
(c) contacting the at least one solid carrier provided in step (a) and the transition metal reagent provided in step (b) to obtain a mixture comprising a solid carrier and a transition metal reagent;
(d) calcining the mixture of step (c) at a temperature between 250° C. and 500° C. for obtaining a catalytic system comprising a transition metal compound on the solid carrier, wherein the transition metal compound is selected from the group consisting of Ni oxides, Ru oxides, Au oxides, Fe oxides, Cu oxides and mixtures thereof; and
(e) optionally reducing the calcined catalytic system obtained from step (d) under $H_2$ atmosphere at a temperature between 100° C. and 500° C. for obtaining a catalytic system comprising a transition metal compound on the solid carrier, wherein the transition metal compound is selected from the group consisting of elemental Ni, elemental Ru, elemental Au, elemental Fe, elemental Cu and mixtures thereof;
(f) providing a solvent and contacting the at least one solid carrier provided in step (a) and/or the transition metal reagent provided in step (b) before or during step (c) in any order; and
(g) removing at least part of the solvent after step (c) and before step (d) by evaporation and/or filtration and/or centrifugation and/or spray drying to obtain a concentrated mixture.

According to another embodiment of the present invention the method for manufacturing the catalytic system comprising the transition metal compound on a solid carrier comprises the steps of:
(a) providing at least one solid carrier, wherein the solid carrier is ground natural calcium carbonate (GNCC) and/or precipitated calcium carbonate (PCC) and has a specific surface area of from 3 to 50 m$^2$/g measured using nitrogen and the BET method according to ISO 9277:2010;
(b) providing at least one transition metal reagent comprising Ni ions, Ru ions, Au ions, Fe ions, Cu ions and mixtures thereof, in such an amount that the amount of said ions is from 0.1 to 30 wt.-%, based on the dry weight of the solid carrier;
(c) contacting the at least one solid carrier provided in step (a) and the transition metal reagent provided in step (b) to obtain a mixture comprising a solid carrier and a transition metal reagent;
(d) calcining the mixture of step (c) at a temperature between 250° C. and 500° C. for obtaining a catalytic system comprising a transition metal compound on the solid carrier, wherein the transition metal compound is selected from the group consisting of Ni oxides, Ru oxides, Au oxides, Fe oxides, Cu oxides and mixtures thereof; and
(e) optionally reducing the calcined catalytic system obtained from step (d) under H$_2$ atmosphere at a temperature between 100° C. and 500° C. for obtaining a catalytic system comprising a transition metal compound on the solid carrier, wherein the transition metal compound is selected from the group consisting of elemental Ni, elemental Ru, elemental Au, elemental Fe, elemental Cu and mixtures thereof;
(f) providing a solvent and contacting the at least one solid carrier provided in step (a) and/or the transition metal reagent provided in step (b) before or during step (c) in any order;
(g) removing at least part of the solvent after step (c) and before step (d) by evaporation and/or filtration and/or centrifugation and/or spray drying to obtain a concentrated mixture; and
(h) thermally treating the mixture of step (c) or the concentrated mixture of step (g) at a temperature between 25° C. and 200° C., preferably at a temperature between 50° C. and 180° C., and most preferably at a temperature between 100° C. to 150° C.

Further Optional Method Steps

The catalytic system obtained by the inventive method is preferably a dry product and most preferably in the form of a powder, flakes, granules, particles, or aggregates.

The obtained catalytic system may optionally be further processed during a grinding step. In general, the grinding of the catalytic system may be performed in a dry or wet grinding process and may be carried out with any conventional grinding device, for example, under conditions such that comminution predominantly results from impacts with a secondary body, i.e. in one or more of: a ball mill, a rod mill, a vibrating mill, a roll crusher, a centrifugal impact mill, a vertical bead mill, an attrition mill, a pin mill, a hammer mill, a pulverizer, a shredder, a de-clumper, a knife cutter, or other such equipment known to the skilled person.

In case the grinding is performed as a wet grinding process, the ground catalytic system may be dried afterwards. In general, the drying may take place using any suitable drying equipment and can, for example, include thermal heating and/or heating at reduced pressure using equipment such as an evaporator, a flash drier, an oven, a spray drier and/or drying in a vacuum chamber. The drying can be carried out at reduced pressure, ambient pressure or under increased pressure. Preferably, the drying is performed at ambient pressure.

The Catalytic System

By the inventive method an inventive catalytic system is obtained. The catalytic system according to the present invention comprises a transition metal compound on a solid carrier, wherein
a) the solid carrier is a ground natural calcium carbonate (GNCC) and/or precipitated calcium carbonate (PCC) and has a specific surface area of from 3 to 50 m$^2$/g measured using nitrogen and the BET method according to ISO 9277:2010; and
b) wherein the transition metal compound is selected from the group consisting of elemental Ni, elemental Ru, elemental Au, elemental Fe, elemental Cu, oxides of the foregoing transition metal compounds and mixtures thereof;
and wherein the content of the transition metal species on the surface of the solid carrier is from 0.1 to 30 wt.-%, based on the dry weight of the solid carrier.

In general, the inventive catalytic system is composed of a particulate solid carrier material (ground natural calcium carbonate and/or precipitated calcium carbonate having a specific surface area of from 3 to 50 m$^2$/g measured using nitrogen and the BET method according to ISO 9277:2010) and a transition metal compound (elemental Ni, elemental Ru, elemental Au, elemental Fe, elemental Cu, oxides of the foregoing transition metal compounds and mixtures thereof) present on at least part of the accessible surface of said carrier material. The transition metal species is present on the surface of the solid carrier from 0.1 to 30 wt.-%, based on the dry weight of the solid carrier.

Specific embodiments of the solid carrier are already described hereinabove under step (a) of the inventive method and shall apply accordingly to the solid carrier and the transition metal compound of the inventive catalytic system.

According to one embodiment, the solid carrier is precipitated calcium carbonate (PCC).

According to another embodiment of the present invention, the solid carrier has:
(i) a specific surface area in the range of from 5 to 40 m$^2$/g, preferably from 7 to 35 m$^2$/g and more preferably from 10 to 30 m$^2$/g, measured using nitrogen and the BET method according to ISO 9277:2010; and
(ii) a $d_{50}$(wt) in the range of from 1 to 75 µm, preferably from 2 to 50 µm, more preferably from 3 to 40 µm, even more preferably from 4 to 30 µm and most preferably from 5 to 15 µm; and
(iii) a $d_{98}$(wt) in the range of from 2 to 150 µm, preferably from 4 to 100 µm, more preferably from 6 to 80 µm, even more preferably from 8 to 60 µm and most preferably from 10 to 30 µm.

According to another embodiment of the present invention, the solid carrier has:
(i) a specific surface area in the range of from 5 to 40 m$^2$/g, preferably from 7 to 35 m$^2$/g and more preferably from 10 to 30 m$^2$/g, measured using nitrogen and the BET method according to ISO 9277:2010; or
(ii) a $d_{50}$(wt) in the range of from 1 to 75 µm, preferably from 2 to 50 µm, more preferably from 3 to 40 µm, even more preferably from 4 to 30 µm and most preferably from 5 to 15 µm; or (iii) a $d_{98}$(wt) in the range of from 2 to 150 µm, preferably from 4 to 100 µm, more preferably from 6 to 80 µm, even more preferably from 8 to 60 µm and most preferably from 10 to 30 µm.

Specific embodiments of the transition metal compound are already described hereinabove under step (d) and (e) of the inventive method and shall apply accordingly to the solid carrier and the transition metal compound of the inventive catalytic system.

According to one embodiment of the present invention, the transition metal compound is preferably selected from the group consisting elemental Ni, NiO, Ni2O3, Ni3O4, elemental Ru, RuO2, Ru2O3, RuO4, elemental Au, Au2O, Au2O3, elemental Fe, FeO, FeO2, Fe2O3, Fe3O4, elemental Cu, CuO, Cu2O, CuO2, Cu2O3 and mixtures thereof, preferably is selected from the group consisting of elemental Ni, NiO, Ni2O3, Ni3O4, elemental Ru, RuO2, Ru2O3, RuO4, elemental Au, Au2O, Au2O3 and mixtures thereof and most preferably is selected from the group consisting of elemental Ru, RuO2, Ru2O3, RuO4 and mixtures thereof.

According to another embodiment of the present invention, the catalytic system further comprises one or more reaction products obtained by reaction of the combination of transition metal compound and the solid carrier.

According to another embodiment of the present invention, the content of the transition metal species on the surface of the solid carrier is in the range of from 0.25 to 25 wt. %, preferably from 0.5 to 20 wt. %, more preferably 1 to 15 wt. %, even more preferably from 2 to 10 wt. % and most preferably from 2.5 to 5 wt. %, based on the dry weight of the solid carrier.

The inventors found that the catalytic system according to the present invention has several advantages. First of all, it has been found that the ground natural calcium carbonate and/or the precipitated calcium carbonate according to the present invention are easily and cheap obtainable materials. Said material have found to be specifically useful as carrier material in catalysis. Especially, it has been found that in combination with the above-mentioned transition metal compound, for example, higher catalytic activities, for example higher glycerol transformation under inert atmosphere, were achieved with the catalytic systems according to the present invention. Moreover, the inventive catalytic system may be easier to recover and higher yields may be achieved.

The catalytic system according to the present invention comprises a transition metal compound on a solid carrier, wherein
a) the solid carrier is a precipitated calcium carbonate (PCC) and has a specific surface area of from 3 to 50 $m^2$/g, preferably from 5 to 40 $m^2$/g, more preferably from 7 to 35 $m^2$/g and most preferably from 10 to 30 $m^2$/g measured using nitrogen and the BET method according to ISO 9277:2010; and
b) wherein the transition metal compound is selected from the group consisting of elemental Ni, elemental Ru, elemental Au, elemental Fe, elemental Cu, oxides of the foregoing transition metal compounds and mixtures thereof;
and wherein the content of the transition metal species on the surface of the solid carrier is from 0.1 to 30 wt.-%, preferably from 0.25 to 25 wt. %, more preferably from 0.5 to 20 wt. %, and even more preferably 1 to 15.-wt. %, based on the dry weight of the solid carrier.

According to an exemplified embodiment of the present invention, the catalytic system according to the present invention comprises a transition metal compound on a solid carrier, wherein
a) the solid carrier is a precipitated calcium carbonate (PCC) and has a specific surface area from 10 to 30 $m^2$/g, preferably about 11.7 $m^2$/g measured using nitrogen and the BET method according to ISO 9277:2010; and
b) wherein the transition metal compound is selected from the group consisting of elemental Ni, elemental Ru, elemental Au, elemental Fe, elemental Cu, oxides of the foregoing transition metal compounds and mixtures thereof;
and wherein the content of the transition metal species on the surface of the solid carrier is from 1 to 15.-wt. %, based on the dry weight of the solid carrier.

According to an exemplified embodiment of the present invention, the catalytic system according to the present invention comprises a transition metal compound on a solid carrier, wherein
a) the solid carrier is a precipitated calcium carbonate (PCC) and has a specific surface area from 10 to 30 $m^2$/g, preferably about 11.7 $m^2$/g measured using nitrogen and the BET method according to ISO 9277:2010; and
b) wherein the transition metal compound is selected from the group consisting of elemental Ni, elemental Ru, elemental Au, oxides of the foregoing transition metal compounds and mixtures thereof;
and wherein the content of the transition metal species on the surface of the solid carrier is from 1 to 15.-wt. %, based on the dry weight of the solid carrier.

According to another exemplified embodiment of the present invention, the catalytic system according to the present invention comprises a transition metal compound on a solid carrier, wherein
a) the solid carrier is a precipitated calcium carbonate (PCC) and has a specific surface area from 10 to 30 $m^2$/g, preferably about 11.7 $m^2$/g measured using nitrogen and the BET method according to ISO 9277:2010; and
b) wherein the transition metal compound is selected from the group consisting of elemental Ni, elemental Fe, elemental Cu, oxides of the foregoing transition metal compounds and mixtures thereof, preferably elemental Ni, elemental Cu, oxides of the foregoing transition metal compounds and mixtures thereof;
and wherein the content of the transition metal species on the surface of the solid carrier is about 10 wt.-%, based on the dry weight of the solid carrier.

According to another exemplified embodiment of the present invention, the catalytic system according to the present invention comprises a transition metal compound on a solid carrier, wherein
a) the solid carrier is a precipitated calcium carbonate (PCC) and has a specific surface area from 10 to 30 $m^2$/g, preferably about 11.7 $m^2$/g measured using nitrogen and the BET method according to ISO 9277:2010; and
b) wherein the transition metal compound is selected from the group consisting of elemental Ni, elemental Cu, oxides of the foregoing transition metal compounds and mixtures thereof, preferably elemental Ni, elemental Cu, oxides of the foregoing transition metal compounds and mixtures thereof;

and wherein the content of the transition metal species on the surface of the solid carrier is about 10 wt.-%, based on the dry weight of the solid carrier.

According to another exemplified embodiment of the present invention, the catalytic system according to the present invention comprises a transition metal compound on a solid carrier, wherein a) the solid carrier is a precipitated calcium carbonate (PCC) and has a specific surface area from 10 to 30 m²/g, preferably about 11.7 m²/g measured using nitrogen and the BET method according to ISO 9277:2010; and b) wherein the transition metal compound is selected from the group consisting of elemental Ru, elemental Au, oxides of the foregoing transition metal compounds and mixtures thereof, preferably elemental Ru and oxides of the foregoing transition metal compound;

and wherein the content of the transition metal species on the surface of the solid carrier is about 1 wt.-%, based on the dry weight of the solid carrier.

Use of the Inventive Catalytic System in Catalysis

According to one aspect of the present invention a solid carrier as described hereinabove that is loaded with a transition metal compound as described hereinabove is used as a catalyst.

The inventive catalytic system was found to be particularly useful in a number of catalytic reactions. For example, higher yields in glycerol transformation under inert atmosphere allowed to obtain high yields of lactic acid known to be a starting materials for numerous products such as the biodegradable polylactic acid were achieved.

One aspect of the present invention therefore relates to the use of the inventive catalytic system in a process comprising the following steps:

(A) providing one or more reactants;
(B) providing the inventive catalytic system;
(C) subjecting the one or more reactants provided in step (A) to a chemical reaction under air, O2 atmosphere, H2 atmosphere or inert atmosphere at a temperature between 75 and 300° C. in the presence of the catalytic system provided in step (B).

For example, the inventive catalytic system may be recovered more easily and higher yields may be achieved in a second catalytic cycle compared with conventional carrier systems, a preferred embodiment of the present invention relates to the use of the inventive catalytic system in a process according to the foregoing aspect, wherein said process further comprises step (D) of recovering the catalytic system following the chemical reaction of step (C) and optionally recycling the catalytic system following the chemical reaction of step (C).

In a preferred embodiment of the present invention, the chemical reaction in step (C) comprises heterogeneous catalysis. In a more preferred embodiment, the chemical reaction in step (C) may be selected from one or more of the following reaction types: hydrogenolysis, C—C couplings and C—C cross couplings, C—N cross couplings, C—O cross couplings, C—S cross couplings, cycloaddition reactions, alkene hydrogenations and alkyne hydrogenations, allylic substitutions, reductions of nitro groups and hydrocarbonylations of aryl halides, preferably hydrogenolysis, C—C couplings and C—C cross couplings.

The inventive catalytic system may also be used in form of different shapes such as granules, mouldings or extrudates comprising said catalytic system. Typical shapes include spheres, minispheres, monoliths, honeycombs, rings, granules, hollow core tablets etc.

Granules are made by crushing and screening gels to obtain the desired size or by drying precipitated pastes together with binders. Optionally, the granulation process further includes heat treatment to achieve specific physical properties. The particle size of granules typically ranges from 40 μm up to 1 cm.

Mouldings are hollow forms having a particular shape obtained from something in a malleable state.

Extrudates are formed by pushing a paste through a die, cutting to length, drying and optional calcining.

The scope and interest of the invention may be better understood on basis of the following examples which are intended to illustrate embodiments of the present invention.

EXAMPLES

1. Measurement Methods

The following measurement methods were used to evaluate the parameters given in the examples and claims.

BET Specific Surface Area (SSA) of a Material

The BET specific surface area was measured via the BET process according to ISO 9277:2010 using nitrogen, following conditioning of the sample by heating at 250° C. for a period of 30 minutes. Prior to such measurements, the sample was filtered, rinsed and dried at 110° C. in an oven for at least 12 hours.

Particle Size Distribution (Weight % Particles with a Diameter <X), $d_{50}$ Value (Weight Median Grain Diameter) and $d_{98}$ Value of a Particulate Material:

The weight median grain diameter is determined by the sedimentation method, which is an analysis of sedimentation behaviour in a gravimetric field. The measurement is made with a Sedigraph™ 5100, Micromeritics Instrument Corporation. The method and the instrument are known to the skilled person and are commonly used to determine grain size of fillers and pigments. The measurement is carried out in an aqueous solution of 0.1 wt % $Na_4P_2O_7$. The samples were dispersed using a high speed stirrer and supersonicated.

The processes and instruments are known to the skilled person and are commonly used to determine grain size of fillers and pigments.

Powder X-Ray Diffraction (XRD)

Powder X-Ray Diffraction (XRD) patterns were recorded on a Bruker D8-Advance X-ray powder diffractometer operated at an accelerating voltage of 40 kV and an emission current of 40 mA with Cu Kα radiation. Samples were scanned over the range of 10°-70°, step size of 0.014° and a time of 0.1 s par step. The setting of 10 mm divergence, fent primaire Soller 2.5° were used.

Three types of catalysts were analysed: dried catalysts, calcined catalysts treated in static air and calcined catalysts treated in static air and reduced under H2 atmosphere.

Two different protocols were applied to prepare the different types of catalysts for XRD analysis. Fresh catalysts and catalysts treated in static air were prepared under ambient atmosphere. Reduced catalysts were prepared in the glove box under inert atmosphere to avoid the oxidation of the metal species during the sample preparation.

The samples were transferred, one by one, and analysed by XRD to avoid the oxidation of metal during sample transfer and analysis.

2. Material and Equipment

Preparation of the Catalytic System

The preparation of the catalysts was performed using 'Chemspeed Catimpreg workstation' designed for automated parallel synthesis of catalysts by coprecipitation and impregnation. In the first stage, a precipitated calcium carbonate (PCC), that is commercial available and has a BET of 11.7 m$^2$/g, a d$_{50}$ of 1.52 µm and a d$_{98}$ of 6.16 µm was dried overnight at 100° C., then distributed in the different glass reactors, followed by adding water into the carrier, then agitating the components at 600 RPM for 5 minutes. The different metal precursor solutions, prepared in water solvent, were added after on the solid carrier, followed by an agitation process at 600 RPM for 60 minutes. The catalysts were next dried at 90° C. under vacuum (950 mbar) over 6 hours. A calcination step under static air was performed at 400° C. for 3 hours, followed by a reduction under a hydrogen flow at 350° C. for 3 hours. The obtained catalysts and the used metal salts used during the preparation procedure are described in the table below:

| Name of the catalyst | Used carrier | Metal salt used for the preparation | Producer | Reference | Theoretical amount of the elemental metal in the final catalyst (wt %) |
|---|---|---|---|---|---|
| Fe, 10%/PCC | PCC | Fe(NO$_3$)$_3$ | Sigma Aldrich | 216828 | 10 |
| Ni, 10%/PCC |  | Ni(NO$_3$)$_2$ | Sigma Aldrich | 72253 | 10 |
| Cu, 10%/PCC |  | Cu(NO$_3$)$_2$ | Sigma Aldrich | 61194 | 10 |
| Ru, 1%/PCC |  | RuNO(NO$_3$)$_3$ | Alfa Aesar | 12175 | 1 |
| Au, 1%/PCC |  | HAuCl$_4$ | Sigma Aldrich | 520918 | 1 |

3. Example Data

Characterization of the Catalytic Systems

XRD measurements of the obtained catalytic systems were performed. X in the below table marks that the phase has been detected by XRD after drying but before calcination (dried), after calcination (calcined) and after calcination+reduction under hydrogen (reduced).

| Sample | Identification of the different phases analysed using XRD technique |||||||||||
|---|---|---|---|---|---|---|---|---|---|---|---|
|  | Aragonite | Calcite | Fe$_2$O$_3$ | Fe | Ni(OH)$_2$ | NiO | Ni$^0$ | CuO | Cu | RuO$_2$ | Ru |
| PCC | X | X | — | — | — | — | — | — | — | — | — |
| Fe, 10%/PCC calcined | X | X | X | — | — | — | — | — | — | — | — |
| Fe, 10%/PCC reduced | X | X | — | X | — | — | — | — | — | — | — |
| Ni, 10%/PCC dried | X | X | — | — | X | — | — | — | — | — | — |
| Ni, 10%/PCC calcined | X | X | — | — | — | X | — | — | — | — | — |
| Ni, 10%/PCC reduced | X | X | — | — | — | X | X | — | — | — | — |
| Cu, 10%/PCC dried | X | X | — | — | — | — | — | X | — | — | — |
| Cu, 10%/PCC calcined | X | X | — | — | — | — | — | X | — | — | — |
| Cu, 10%/PCC reduced | X | X | — | — | — | — | — | — | X | — | — |
| Ru, 1%/PCC dried | X | X | — | — | — | — | — | — | — | — | — |
| Ru, 1%/PCC calcined | X | X | — | — | — | — | — | — | — | X | — |
| Ru, 1%/PCC reduced | X | X | — | — | — | — | — | — | — | — | X |

Catalytic Investigations

The obtained catalysts were evaluated in three different type of chemical transformations, using glycerol as a starting molecule. Glycerol chemical transformations were performed under hydrogen or inert atmosphere (nitrogen) or oxygen atmospheres. The procedure was performed using a Screening Pressure Reactor (SPR) from Unchained Labs, which is an automated high-throughput reactors system.

In a first step, the reactors were filled with the catalyst, glycerol and sodium hydroxide reagents. The reactors were next purged with nitrogen while mixing its contents, to eliminate air. Then the required atmosphere was replaced, followed by heating the reactors to the desired temperatures.

The performed reactivity tests are described in the table below:

| Atmosphere | Pressure (bar) | Temperature (° C.) | Time (hours) | NaOH/Gly molar ratio |
|---|---|---|---|---|
| $H_2$ | 30 | 200 | 6 | 1.5 |
|  |  |  | 12 |  |
| $N_2$ | 30 | 200 | 6 |  |
|  |  |  | 12 |  |
| 40% $O_2$/60% $N_2$ | 7.5 | 80 | 4 | 4 |

For the identification of the products obtained during the catalytic reaction, HPLC-UV liquid chromatograph from Shimadzu equipped with UV detector SPD-20A ($\lambda$=210 nm), pumps LC-30AD coupled with Waytt Refractive Index (RI) detector (Optilab T-rEX) were used for the qualitative and quantitative analysis of the products. A calibration of all the potentially obtained products was performed, for a precise quantification. HPLC analysis were carried out using a LC column Bio-Rad Aminex HPX-87H, operated at 60° C. A 0.01N $H_2SO_4$ aqueous solution was used as the mobile phase. Products were analysed at a flow rate of 0.5 mL/min.

The results obtained using the different catalysts under a reductive atmosphere are presented in the table below:

| Used catalyst | Experimental conditions | Glycerol/Metal molar ratio | Glycerol conv. (%) | Lactic acid | 1,2-Propanediol | Methanol | Ethanol | Carbon balance |
|---|---|---|---|---|---|---|---|---|
| Fe, 10%/PCC | 200° C., 6 hours, $H_2$ 30 bar, NaOH/Gly of 1.5 | 106 | 4.6 | 1.7 | 0.0 | 0.0 | 0.0 | 97.1 |
|  | 200° C., 12 hours, $H_2$ 30 bar, NaOH/Gly of 1.5 |  | 11.9 | 1.9 | 0.0 | 0.0 | 0.0 | 90.0 |
| Ni, 10%/PCC | 200° C., 6 hours, $H_2$ 30 bar, NaOH/Gly of 1.5 | 107 | 100 | 41.7 | 23.6 | 15.8 | 7.0 | 93.1 |
|  | 200° C., 12 hours, $H_2$ 30 bar, NaOH/Gly of 1.5 |  | 100 | 36.7 | 22.3 | 10.9 | 5.2 | 78.7 |
| Cu, 10%/PCC | 200° C., 6 hours, $H_2$ 30 bar, NaOH/Gly of 1.5 | 105 | 6.0 | 3.1 | 0.0 | 0.0 | 0.0 | 97.2 |
|  | 200° C., 12 hours, $H_2$ 30 bar, NaOH/Gly of 1.5 |  | 5.9 | 2.2 | 0.0 | 0.0 | 0.0 | 96.2 |
| Ru, 1%/PCC | 200° C., 6 hours, $H_2$ 30 bar, NaOH/Gly of 1.5 | 1462 | 18.4 | 12.5 | 1.1 | 0.0 | 0.0 | 95.5 |
|  | 200° C., 12 hours, $H_2$ 30 bar, NaOH/Gly of 1.5 |  | 23.9 | 16.9 | 1.5 | 0.0 | 0.0 | 94.6 |
| Au, 1%/PCC | 200° C., 6 hours, $H_2$ 30 bar, NaOH/Gly of 1.5 | 1555 | 5.9 | 3.5 | 0.0 | 0.0 | 0.0 | 97.6 |
|  | 200° C., 12 hours, $H_2$ 30 bar, NaOH/Gly of 1.5 |  | 7.7 | 4.2 | 0.0 | 0.0 | 0.0 | 96.5 |

[a]The remaining products up to 100% are only detected but in limited amounts and, therefore, are not presented in this table.

The results obtained using the different catalysts under an inert atmosphere are presented in the table below:

| Used catalyst | Experimental conditions | Glycerol/Metal molar ratio | Glycerol conv. (%) | Lactic acid | 1,2-Propanediol | Methanol | Ethanol | Carbon balance |
|---|---|---|---|---|---|---|---|---|
| Fe, 10%/PCC | 200° C., 6 hours, $N_2$ 30 bar, NaOH/Gly of 1.5 | 106 | 3.8 | 1.9 | 0.0 | 0.0 | 0.0 | 98.0 |
|  | 200° C., 12 hours, $N_2$ 30 bar, NaOH/Gly of 1.5 |  | 5.1 | 3.8 | 0.0 | 0.0 | 0.0 | 98.7 |
| Ni, 10%/PCC | 200° C., 6 hours, $N_2$ 30 bar, NaOH/Gly of 1.5 | 107 | 100 | 47.7 | 11.5 | 9.8 | 4.4 | 78.6 |
|  | 200° C., 12 hours, $N_2$ 30 bar, NaOH/Gly of 1.5 |  | 100 | 61.6 | 0.0 | 4.6 | 4.3 | 74.7 |
| Cu, 10%/PCC | 200° C., 6 hours, $N_2$ 30 bar, NaOH/Gly of 1.5 | 105 | 4.5 | 2.4 | 0.0 | 0.0 | 0.0 | 98.1 |
|  | 200° C., 12 hours, $N_2$ 30 bar, NaOH/Gly of 1.5 |  | 88.9 | 78.9 | 2.5 | 0.7 | 0.0 | 97.0 |

-continued

| Used catalyst | Experimental conditions | Glycerol/Metal molar ratio | Glycerol conv. (%) | Lactic acid | 1,2-Propanediol | Methanol | Ethanol | Carbon balance |
|---|---|---|---|---|---|---|---|---|
| Ru, 1%/PCC | 200° C., 6 hours, N₂ 30 bar, NaOH/Gly of 1.5 | 1462 | 37.9 | 30.5 | 2.2 | 4.5 | 0.0 | 100.9 |
|  | 200° C., 12 hours, N₂ 30 bar, NaOH/Gly of 1.5 |  | 74.4 | 69.0 | 2.4 | 0.7 | 0.0 | 102.4 |
| Au, 1%/PCC | 200° C., 6 hours, N₂ 30 bar, NaOH/Gly of 1.5 | 1555 | 5.7 | 4.4 | 0.0 | 0.0 | 0.0 | 98.7 |
|  | 200° C., 12 hours, N₂ 30 bar, NaOH/Gly of 1.5 |  | 14.3 | 10.9 | 0.0 | 0.0 | 0.0 | 96.8 |

$^a$The remaining products up to 100% are only detected in limited amounts and, therefore, are not presented in this table.

The results obtained using the different catalysts under an oxidative atmosphere are presented in the table below:

| Used catalyst | Experimental conditions | Glycerol/Metal molar ratio | Glycerol conv. (%) | Glyceric acid | Glycolic acid | Lactic acid | Formic acid | 1,2-Propanediol | Carbon balance |
|---|---|---|---|---|---|---|---|---|---|
| Fe, 10%/PCC | 100° C., 4 hours, 40% O₂ at 17 bar, NaOH/Gly of 4 | 106 | 6.8 | 0.2 | 1.7 | 2.3 | 0.9 | 0.0 | 98.3 |
| Ni, 10%/PCC | 100° C., 4 hours, 40% O₂ at 17 bar, NaOH/Gly of 4 | 107 | 8.3 | 0.5 | 1.2 | 5.5 | 0.9 | 3.7 | 104.9 |
| Cu, 10%/PCC | 100° C., 4 hours, 40% O₂ at 17 bar, NaOH/Gly of 4 | 105 | 5.1 | 0.3 | 1.3 | 2.7 | 0.9 | 0.0 | 100.1 |
| Ru, 1%/PCC | 100° C., 4 hours, 40% O₂ at 17 bar, NaOH/Gly of 4 | 1462 | 3.1 | 0.3 | 1.0 | 3.1 | 0.9 | 0.0 | 102.3 |
| Au, 1%/PCC | 100° C., 4 hours, 40% O₂ at 17 bar, NaOH/Gly of 4 | 1555 | 4.5 | 0.3 | 1.3 | 2.1 | 0.8 | 0.0 | 100.0 |

$^a$The remaining products are only detected in limited amounts and, therefore, are not presented in this table.

As can be seen from the above experimental data, by the inventive method it is possible to provide catalytic systems wherein the transition metal compound that is selected from the group consisting of elemental Ni, elemental Ru, elemental Au, elemental Fe, elemental Cu, oxides of the foregoing transition metal compounds and mixtures thereof is located on the solid carrier, which is a ground natural calcium carbonate (GNCC) and/or precipitated calcium carbonate (PCC) and has a specific surface area of from 3 to 50 m²/g measured using nitrogen and the BET method according to ISO 9277:2010. Furthermore, the inventive method is a cheap and simple production process which provides the inventive catalytic system.

Additionally, as can be seen from the above experimental data the precipitated calcium carbonate is useful as carrier material for specific transition metal compounds in the catalysis. Furthermore, it can be seen that for the inventive catalytic system high catalytic activities, for example high glycerol transformation under inert atmosphere, hydrogen or oxygen were achieved as well as a targeted selectivity to a well-defined product, namely lactic acid.

The invention claimed is:
1. A catalytic system comprising:
 at least one solid carrier and a transition metal compound on the at least one solid carrier, wherein
 the at least one solid carrier is a ground natural calcium carbonate (GNCC) and/or precipitated calcium carbonate (PCC) and has a specific surface area of from 3 to 50 m²/g measured using nitrogen and the BET method according to ISO 9277:2010, wherein the ground natural calcium carbonate and/or precipitated calcium carbonate is not a surface-reacted calcium carbonate; and
 wherein the transition metal compound is selected from the group consisting of elemental Ni, elemental Ru, elemental Au, elemental Fe, elemental Cu, oxides of the foregoing transition metal compounds and mixtures thereof;
 and wherein the content of a transition metal species on the surface of the at least one solid carrier is from 0.1 to 30 wt.-%, based on the dry weight of the solid carrier.
2. The catalytic system according to claim 1, wherein the at least one solid carrier is precipitated calcium carbonate (PCC) and/or wherein the at least one solid carrier has:
 (i) a specific surface area in the range of from 5 to 40 m²/g; and/or
 (ii) a $d_{50}$(wt) in the range of from 1 to 75 μm; and/or
 (iii) a $d_{98}$(wt) in the range of from 2 to 150 μm.
3. The catalytic system according to claim 2, wherein the at least one solid carrier is precipitated calcium carbonate (PCC) and/or wherein the at least one solid carrier has:
 (i) a specific surface area in the range of 10 to 30 m²/g, measured using nitrogen and the BET method according to ISO 9277:2010; and/or
 (ii) a $d_{50}$(wt) in the range of from 5 to 15 μm; and/or
 (iii) a $d_{98}$(wt) in the range of from 10 to 30 μm.
4. The catalytic system according to claim 1, wherein the transition metal compound is selected from the group consisting of elemental Ni, NiO, Ni₂O₃, Ni₃O₄, elemental Ru, RuO₂, Ru₂O₃, RuO₄, elemental Au, Au₂O, Au₂O₃, elemental Fe, FeO, FeO₂, Fe₂O₃, Fe₃O₄, elemental Cu, CuO, Cu₂O, CuO₂, Cu₂O₃ and mixtures thereof.
5. The catalytic system according to claim 4, wherein the transition metal compound is selected from the group consisting of elemental Ru, RuO₂, Ru₂O₃, RuO₄ and mixtures thereof.
6. The catalytic system according to claim 1, wherein the catalytic system further comprises one or more reaction products obtained by reaction of the combination of transition metal compound and the solid carrier.

7. The catalytic system according to claim 1, wherein the content of the transition metal species on the surface of the solid carrier is in the range of from 0.25 to 25 wt. %, based on the dry weight of the solid carrier.

8. The catalytic system according to claim 7, wherein the content of the transition metal species on the surface of the solid carrier is in the range of from 2.5 to 5 wt. %, based on the dry weight of the solid carrier.

9. A method of using a catalytic system according to claim 1 in a process comprising:
   (A) providing one or more reactants;
   (B) providing said catalytic system;
   (C) subjecting the one or more reactants provided in step (A) to a chemical reaction in liquid or gas phase under air, $O_2$ atmosphere, $H_2$ atmosphere, or inert atmosphere at a temperature between 75 and 300° C. in the presence of the catalytic system provided in step (B).

10. The method according to claim 9, wherein the process further comprises a step (D) of recovering and optionally recycling the catalytic system following the chemical reaction of step (C).

11. A catalyst comprising the catalyst system according to claim 1.

12. Granules, mouldings or extrudates comprising the catalytic system according to claim 1.

13. A method for manufacturing a catalytic system comprising at least one solid carrier and a transition metal compound on the solid carrier, the method comprising:
   (a) providing the at least one solid carrier, wherein the at least one solid carrier is ground natural calcium carbonate (GNCC) and/or precipitated calcium carbonate (PCC) and has a specific surface area of from 3 to 50 $m^2/g$ measured using nitrogen and the BET method according to ISO 9277:2010, wherein the ground natural calcium carbonate and/or precipitated calcium carbonate is not a surface-reacted calcium carbonate;
   (b) providing at least one transition metal reagent comprising Ni ions, Ru ions, Au ions, Fe ions, Cu ions and mixtures thereof, in such an amount that the amount of said ions is from 0.1 to 30 wt.-%, based on the dry weight of the solid carrier;
   (c) contacting the at least one solid carrier provided in step (a) and the transition metal reagent provided in step (b) to obtain a mixture comprising a solid carrier and a transition metal reagent; and
   (d) calcining the mixture of step (c) at a temperature between 250° C. and 500° C. to obtain the catalytic system comprising a transition metal compound on the at least one solid carrier, wherein the transition metal compound is selected from the group consisting of Ni oxides, Ru oxides, Au oxides, Fe oxides, Cu oxides and mixtures thereof.

14. The method according to claim 13, wherein the method further comprises a step (e) of reducing the calcined catalytic system obtained from step (d) under H2 atmosphere at a temperature between 100° C. and 500° C. to obtain the catalytic system comprising a transition metal compound on the at least one solid carrier, wherein the transition metal compound is selected from the group consisting of elemental Ni, elemental Ru, elemental Au, elemental Fe, elemental Cu, oxides of the foregoing transition metal compounds and mixtures thereof.

15. The method according to claim 13, wherein the calcining step (d) is performed
   (i) under air, $N_2$ atmosphere, Ar atmosphere, $O_2$ atmosphere or mixtures thereof, and/or
   (ii) at a temperature between 270° C. and 480° C.

16. The method according to claim 13, wherein the method further comprises a step of:
   (f) providing a solvent and contacting the at least one solid carrier provided in step (a) and/or the transition metal reagent provided in step (b) before or during step (c) in any order; and
   optionally further comprises a step of (g) removing at least part of the solvent after step (c) and before step (d) by evaporation and/or filtration and/or centrifugation and/or spray drying to obtain a concentrated mixture.

17. The method according to claim 16, wherein the method further comprises step (h) of thermally treating the mixture of step (c) or the concentrated mixture of step (g) at a temperature between 25° C. and 200° C.

18. The method according to claim 16, wherein the solvent is a non-polar solvent, a polar solvent or a mixture thereof, and wherein the non-polar solvent is selected from the group consisting of pentane, cyclopentane, hexane, cyclohexane, benzene, toluene, 1,4-dioxane, chloroform, diethyl ether, dichloromethane and mixtures thereof and/or the polar solvent is selected from the group consisting of tetrahydrofuran, ethyl acetate, acetone, dimethylformamide, acetonitrile, dimethyl sulphoxide, nitromethane, propylene carbonate, formic acid, n-butanol, isopropanol, n-propanol, ethanol, methanol, acetic acid, water and mixtures thereof.

19. The method according to claim 18 wherein the solvent is water.

20. The method according to claim 13, wherein the transition metal reagent is selected from the group consisting of $(NH_4)_2Ni(SO_4)_2$, $Ni(OCOCH_3)_2$, $NiBr_2$, $NiCl_2$, $NiF_2$, $Ni(OH)_2$, $NiI_2$, $Ni(NO_3)_2$, $Ni(ClO_4)_2$, $Ni(SO_3NH_2)_2$, $NiSO_4$, $K_2Ni(H_2O_6)_2$, $K_2Ni(CN)_4$, $[Ru(NH_3)_6]Cl_2$, $[Ru(NH_3)_6]Cl_3$, $[Ru(NH_3)_5Cl]Cl_2$, $RuCl_3$, $RuI_3$, $RuF_5$, $Ru(NO)(NO_3)_3$, $HAuCl_4$, $AuBr_3$, $AuCl$, $AuCl_3$, $Au(OH)_3$, $AuI$, $KAuCl_4$, $Cu_2S$, copper(I)-thiophene-2-carboxylate, $CuBr$, $CuCN$, $CuCl$, $CuF$, $CuI$, $CuH$, $CuSCN$, $CuBr_2$, $CuCO_3$, $CuCl_2$, $CuF_2$, $Cu(NO_3)_2$, $Cu_3(PO_4)_2$, $Cu(OH)_2$, $CuI_2$, $CuS$, $CuSO_4$, $Cu_2(OAc)_4$, $(NH_4)_2Fe(SO_4)_2$, $FeBr_2$, $FeBr_3$, $FeCl_2$, $FeCl_3$, $FeF_2$, $FeF_3$, $FeI_2$, $Fe(NO_3)_3$, $FeC_2O_4$, $Fe_2(C_2O_4)_3$, $Fe(ClO_4)_2$, $FePO_4$, $FeSO_4$, $Fe(BF_4)_2$, $K_4Fe(CN)_6$ and mixtures thereof.

* * * * *